US010150974B2

(12) United States Patent
Green et al.

(10) Patent No.: US 10,150,974 B2
(45) Date of Patent: Dec. 11, 2018

(54) SOLVENT PRODUCTION

(71) Applicant: GREEN BIOLOGICS LIMITED, Abdingdon Oxfordshire (GB)

(72) Inventors: Edward Green, Bisham (GB); Ross Patrick Simms, Midlothian, VA (US); Carl-Axel Magnusson Lalander, Didcot (GB); Rosa Maria Dominguez-Espinosa, Earley (GB)

(73) Assignee: GREEN BIOLOGICS LIMITED, Oxfordshire (GB)

(*) Notice: Subject to any disclaimer, the term of this patent is extended or adjusted under 35 U.S.C. 154(b) by 77 days.

(21) Appl. No.: 14/900,302

(22) PCT Filed: Jun. 27, 2014

(86) PCT No.: PCT/GB2014/051972
§ 371 (c)(1),
(2) Date: Dec. 21, 2015

(87) PCT Pub. No.: WO2014/207480
PCT Pub. Date: Dec. 31, 2014

(65) Prior Publication Data
US 2017/0067082 A1 Mar. 9, 2017

Related U.S. Application Data

(60) Provisional application No. 61/841,077, filed on Jun. 28, 2013.

(30) Foreign Application Priority Data

Aug. 30, 2013 (GB) .................................. 1315475.2

(51) Int. Cl.
*C12P 7/16* (2006.01)
*C12R 1/145* (2006.01)
*C12P 7/02* (2006.01)
*C09K 3/00* (2006.01)

(52) U.S. Cl.
CPC .................... *C12P 7/16* (2013.01); *C09K 3/00* (2013.01); *C12P 7/02* (2013.01); *C12R 1/145* (2013.01); *Y02E 50/10* (2013.01); *Y02E 50/17* (2013.01)

(58) Field of Classification Search
None
See application file for complete search history.

(56) References Cited

U.S. PATENT DOCUMENTS

| 7,851,188 B2 | 12/2010 | Donaldson et al. |
| 8,101,808 B2 | 1/2012 | Evanko et al. |
| 8,900,841 B2 | 12/2014 | Medoff et al. |
| 9,074,173 B2 | 7/2015 | Walther et al. |
| 2007/0207531 A1 | 9/2007 | Ferchichi et al. |
| 2009/0162912 A1 | 6/2009 | Ezeji et al. |
| 2010/0330633 A1 | 12/2010 | Cobalt |
| 2011/0162953 A1 | 7/2011 | Xu et al. |
| 2013/0149757 A1 | 6/2013 | Day et al. |
| 2015/0005484 A1 | 1/2015 | Kubo |

FOREIGN PATENT DOCUMENTS

| CN | 101397576 A | 4/2009 |
| CN | 102286549 A | 12/2011 |
| CN | 102703493 B | 8/2016 |
| DE | 3905624 A1 | 9/1990 |
| FR | 2583060 A1 | 12/1986 |
| JP | 2005-328801 A | 12/2005 |
| JP | 2016-096764 A | 5/2016 |
| JP | 2017-051185 A | 3/2017 |
| WO | WO 2007/148091 | 12/2007 |
| WO | WO 2009/101400 | 8/2009 |
| WO | WO 2009/106835 | 9/2009 |
| WO | 101440381 B | 6/2011 |
| WO | WO 2013/027282 | 2/2013 |
| WO | 2017/043656 A1 | 3/2017 |

OTHER PUBLICATIONS

Richter et al., Biotechnology and Bioengineering, 2012, vol. 109, No. 4, p. 913-921, and Supplementary Materials & Tables, p. 1-12, published online Nov. 2011.*
Qureshi et al., Biotechnol. Prog., 1992, vol. 8, p. 382-390.*
Annous, B.A., Blaschek, H.P., "Isolation and characterization of Clostridium acetobutylicum mutants with enhanced amylolytic activity." Appl. Environ. Microbiol., 57(9), 2544-8. 1991.
Baba, S., et al.,"Development of high-speed and highly efficient butanol production systems from butyric acid with high density of living cells of Clostridium saccharoperbutylacetonicum.", J. Biotechnol., 157(4), 605-12. 2012.
Brown, S.D., et al, "Mutant alcohol dehydrogenase leads to improved ethanol tolerance in Clostridium thermocellum," Proc Natl Acad Sci USA, 108(33), 13752-7. 2011.
Dunning and Lathrop "The saccharification of agricultural residues: A continuous process", Ind. Eng. Chem. vol. 37, No. 1, pp. 24-29. 1945.
Ezeji, T.C., et al., "Production of acetone, butanol and ethanol by Clostridium beijerinckii BA101 and in situ recovery by gas stripping," World J. Microbiol. Biotechnol., 19, 595-603. 2003.

(Continued)

*Primary Examiner* — Kade Ariani
(74) *Attorney, Agent, or Firm* — Knobbe Martens Olson & Bear LLP

(57) ABSTRACT

The invention relates to a process and system for the production of a solvent using monophasic solventogenic Clostridia in a single stage process. More particularly, the process and system relate to the use of a culture vessel for culturing monophasic solventogenic Clostridia, wherein cell growth of the *Clostridium* is monitored and optimized by the addition of controlled amounts of culture media and/or the removal of controlled amounts of solvent. The process and system may particularly be used to produce solvents such as butanol, acetone and ethanol.

19 Claims, 12 Drawing Sheets

(56) References Cited

OTHER PUBLICATIONS

Ezeji, T.C. et al., "Improving performance of a gas stripping-based recovery system to remove butanol from Clostridium beijerinckii fermentation"; Bioprocess Biosyst Eng; Springer, Berlin, DE, vol. 27, 207-214, 2005.

Ezeji T C. et al., "Bioproduction of butanol from biomass: from genes to bioreactors"; Current opinion in Biotechnology, London, GB: vol. 18, No. 3, Jun. 8, 2007, pp. 220-227.

Ezeji, T.C., et al., "Microbial production of a biofuel (acetone-butanol-ethanol) in a continuous bioreactor: impact of bleed and simultaneous product removal," Bioprocess Biosyst Eng. Jun. 23, 2012. [Epub ahead of print].

Formanek, J. et al., "Enhanced butanol production by Clostridium beijerinckii BA101 grown in semidefined P2 medium containing 6 percent maltodextrin or glucose," Applied & Environmental Microbiology; vol. 63, pp. 2306-2310, 1997.

Gapes, J.R., et al., "Long-Term Continuous Cultivation of Clostridium beijerinckii in a Two-Stage Chemostat with On-Line Solvent Removal," Appl. Environ. Microbiol., 62(9), 3210-3219. 1996.

Green, E.M., "Fermentative production of butanol—The industrial perspective," Current Opinion in Biotechnology; Jun. 2011, vol. 22, No. 3, pp. 337-343.

Groot, et al., "Technologies for butanol recovery integrated with fermentations," Process Biochemistry, 27, 61-75. 1992.

Harris, E., et al., "Reaction of Hardwood Lignin with Hydrogen", Communication from the US Forest Products Laboratory, (1938) vol. 60, pp. 1467-1470.

Harris, L., et al., 2000, Characterization of recombinant strains of the Clostridium . . . , Biotechnology & Bioengineering; vol. 67, pp. 1-11.

Hayashida, S. & Yoshino, S., "Degeneration of solventogenic Clostridium caused by a defect in Nadh generation." Agric. Biol. Chem., 54(2), 427-435, 1990.

Jang, Y.S., et al., "Enhanced Butanol Production Obtained by Reinforcing the Direct Butanol-Forming Route in Clostridium acetobutylicum," mBIO 3(5). doi:10.1128/mBio.00314-12. 2012.

Jones, D.T. & Woods, D.R., "Acetone-butanol fermentation revisited." Microbiol. Rev., 50(4), 484-524. 1986.

Kashket, E.R., & Cao, Z.Y. "Clostridial strain degeneration," FEMS Microbiol. Rev., 17, 307-315. 1995.

Keis, S. et al., "Emended descriptions of Clostridium acetobutylicum and Clostridium beijerinckii, and descriptions of *Clostridium saccharoperbutylacetonicum* sp. nov. and *Clostridium saccharobutylicum* sp. nov.," Int. J. Systemic Evol. Microbiol. (2001) 51:2095-2103.

Kosaka, T. et al., "Characterization of the sol operon in butanol-heryproducing closridium saccharoperbutylacetonicum strain N1-4 and its degeneration mechanism," Biosci. Biotechnol. Biochem. 71(1) 58-68 (2007).

Maddox, I.S., "The acetone-butanol-ethanol fermentation: recent progress in technology,"Biotechnol. Gen. Eng. Rev., 7, 189-220. 1989.

Maddox, I.S. et al., "Utilization of whey by clostridia and process technology," In: The Clostridia and Biotechnology. D.R. Woods, ed. Butterworth-Heinemann, Boston. p. 343-369. 1993.

Mariano et al., "An alternative Process for Butanol Production: Continuous Flash Fermentation," Univ. of Campinas, 2008, vol. 3, Issue 1, Art 34.

Mariano, A.P., et al., "Bioproduction of butanol in bioreactors: New insights from simultaneous in situ butanol recovery to eliminate product toxicity," Biotechnol Bioeng. Mar. 2, 2011. doi: 10.1002/bit.23123. [Epub ahead of print].

Meyer, C.L., & Papoutsakis, E.T., "Continuous and biomass recycle fermentations of Clostridium acetobutylicum, Part 1: ATP supply and demand determines product selectivity," Bioprocess Eng 4(1), 1-10. 1989.

Minier, et al., "Extractive acetonobutylic fermentation by coupling ultrafiltration and distillation," Biotech. Bioeng. 35:861-9 (1990).

Minier, et al., "Inactivation of lytic enzymes by heat treatment in ultrafiltration-coupled acetonobutylic fermentation," Appl. Microbiol. Biotechnol. 33, 272-279 (1990).

Mutschlechner, O., et al., "Continuous two-stage ABE-fermentation using Clostridium beijerinckii NRRL B592 operating with a growth rate in the first stage vessel close to its maximal value," J. Mol. Microbiol. Biotechnol., 2(1), 101-5. 2000.

Ni, Y., & Sun, Z., "Recent progress on industrial fermentative production of acetone-butanol-ethanol by Clostridium acetobutylicum in China," Appl. Microbiol. Biotechnol., 83, 415-423. 2009.

Qureshi, N., & Maddox, I.S., "Continuous solvent production from whey permeate using cells of Clostridium acetobutylicum immobilized by absorption onto bonechar," Enz. Microb. Technol., 9(11), 668-671. 1987.

Qureshi, N. & Blaschek H.P., "Recent advances in ABE fermentation: hyper-butanol producing Clostridium beijerinckii BA101," Journal of Industrial Microbiology & Biotechnology; vol. 27, pp. 287-291. 2001.

Richter, H., Qureshi, N., Heger, S., Dien, B., Cotta, M.A., & Angenent, L.T., Prolonged conversion of n-butyrate to n-butanol with Clostridium saccharoperbutylacetonicum in a two-stage continuous culture with in-situ product removal.Biotechnol Bioeng. 109(4), 913-921. 2012.

Roffler et al, Berkeley Univ., In-situ Recovery of Fermentation Products; Trends in Biotechnology, vol. 2:5.

Schlote, D., & Gottschalk, G. Effect of cell recycle on continuous butanol-acetone fermentation with Clostridium acetobutylicum under phosphate limitation.Appl. Microbiol. Biotechnol., 24, 1-5. 1986.

Shao, X., Raman, B., Zhu, M., Mielenz, J.R., Brown, S.D., Guss, A.M., & Lynd, L.R.Mutant selection and phenotypic and genetic characterization of ethanol-tolerant strains of Clostridium thermocellum. Appl Microbiol Biotechnol. 92(3), 641-52. 2011.

Syed, Biochemical studies on anaerobic fermentation of molasses by Clostridium acetobutylicum. Ph.D. Thesis. Institute of Chemistry. University of the Punjab. India. 1994.

Thang, V.H., Kanda, K., & Kobayashi, G., Production of Acetone-Butanol-Ethanol (ABE) in Direct Fermentation of Cassava by Clostridium saccharoperbutylacetonicum N1-4.Appl. Biochem. Biotechnol., 161(1-8), 157-70. 2010.

van der Merwe, A.B.Evaluation of Different Process Designs for Biobutanol Production from Sugarcane Molasses.M.Sc. Thesis. University of Stellenbosch, South Africa. 2010.

Van Hecke, W., Vandezande, P., Claes, S., Vangeel, S., Beckers, H., Diels, L., & De Wever. H. Integrated bioprocess for long-term continuous cultivation of Clostridium acetobutylicum coupled to pervaporation with PDMS composite membranes. Bioresour. Technol., 111, 368-77. 2012.

Woolley, R.C. & Morris, J.G. Stability of solvent production by Clostridium acetobutylicum in continuous culture: strain differences J. Appl. Bacteriol., 69(5), 718-728. 1990.

Yang, S., Land, M.L., Klingeman, D.M., Pelletier, D.A., Lu, T.Y., Martin, S.L., Guo, H.B., Smith, J.C., & Brown, S.D.Paradigm for industrial strain improvement identifies sodium acetate tolerance loci in Zymomonas mobilis and *Saccharomyces cerevisiae*. Proc Natl Acad Sci U S A., 107(23), 10395-400. 2010.

Zheng, J., Tashiro, Y., Yoshida, T., Gao, M., Wang, Q., & Sonomoto, K., Continuous butanol fermentation from xylose with high cell density by cell recycling system. Bioresource Technology, 129, 360-365, 2013.

UK Search Report dated Mar. 31, 2014 and Combined Search and Examination Report dated Apr. 1, 2014 in application No. GB1315475.2.

UK Search Report dated Mar. 5, 2015 and Combined Search and Examination Report dated Mar. 6, 2015 in application No. GB1411516.6.

International Search Report dated Jan. 9, 2015 with Written Opinion in application No. PCT/GB2014/051972.

Sivagnanam K, Raghavan VGS, Shah M, Hettich RL, Verberkmoes NC, et al. (2012) Characterization of Clostridium Acetobutylicum Protein Interaction Network from Butanol Fermentation. J Anal Bioanal Techniques S3:002.

Soni et al. "Bioconversion of agro-wastes into acetone butanol", Biotech. Letters, vol. 4, No. 1, pp. 19-22 1982.

(56) References Cited

OTHER PUBLICATIONS

Soni et al. "Inhibitory factors involved in acetone-butanol fermentation by *Clostridium-saccharoperbutylacetonicum*", Current Microbiology, vol. 16, No. 2, pp. 61-68, 1987.

* cited by examiner

SOLVENT PRODUCTION

The invention relates to a process and system for the production of a solvent using monophasic solventogenic clostridia in a single stage process. More particularly, the process and system relate to the use of a culture vessel for culturing monophasic solventogenic clostridia, wherein cell growth of the *clostridium* is monitored and optimized by the addition of controlled amounts of culture media and/or the removal of controlled amounts of solvent. The process and system may particularly be used to produce solvents such as butanol, acetone and ethanol.

The butanol fermentation process utilises renewable bio-based feedstocks and is often referred to as the acetone, butanol and ethanol (ABE) fermentation after its major chemical products. The fermentation was first commercialised in the UK in 1916 and spread around the globe during the 1st and 2nd world wars, mainly to produce acetone for munitions and butanol for paint lacquers. The process fell out of favour in the US and EU in the 1950s when it struggled to compete with petro-derived equivalents on cost, but persisted in China, Russia and South Africa until the 1980s. Today, due to higher oil prices, concerns over the supply of oil and environmental concerns over greenhouse gas (GHG) emission, the ABE fermentation is poised for re-commercialisation. The fermentation route has the potential to replace petro-derived butanol, acetone and hydrogen with cheaper, more sustainable and environmentally-friendly chemicals. Indeed, global demand for bio-butanol has been stimulated by investment in new plant in China. Over $200 m has been invested to date, resulting in 0.3M t/yr of installed solvent capacity with plans to expand to 1M t/yr.

Traditional batch processes for the fermentation of molasses and/or starch to produce ABE have been practised for decades (Jones, D. T. and Woods, D. R. (1986) Microbiol. Rev. 50: 484-524). Typically, batch fermentation produces approximately 18 g/L solvent in 72 hours. The fermentation is relatively long because it occurs in two distinct stages (biphasic): the first phase is a growth stage that results in acid production and a drop in pH; the second phase is a survival stage during which the acids are re-assimilated to solvents to neutralise the pH. The cells also prepare for sporulation. The switch in metabolism is triggered by the acid concentration in the fermentation broth and/or the drop in pH. The final solvent titres are relatively low in comparison with yeast ethanol fermentations, and this results in low volumetric productivities (18/72 which equates to approximately 0.25 g solvent/L/hr). Solvent titres are limited by the relatively low amounts of sugar that can be fermented. Low solvent productivities are a major drawback with the traditional batch process and many attempts have been made to overcome this limitation.

Variations on batch culture processes including fed-batch processes which attempt to either increase solvent titre or to reduce the fermentation time have been developed with little success.

Due to the low productivity obtained with batch fermentation processes, several single-stage continuous processes have been proposed (e.g. Jones and Woods (1986), supra) which aim to provide a continuous flow of feed media in order to achieve a growth rate close to the maximum growth rate for several weeks, thus offering improving solvent production rates and reduced downtime. However, in practice, this is difficult to achieve with biphasic solventogenic clostridia because solvent production is not directly linked to growth and cultures wash out at relatively low dilution rates. Methods of retaining high cell concentrations in the reactor using cell-recycling and/or immobilization have been demonstrated at lab-scales, but are difficult to implement on commercial scales (e.g. Qureshi & Maddox (1987), Enz. Microb. Technol. 9(11), 668-67; Maddox (1989) Gen. Eng. Rev., 7, 189-220; Maddox et al. (1993) In: The clostridia and biotechnology, (eds) D. R. Woods, Butterworth-Heinemann, Boston. 343-369; Gapes et al. (1996) Appl. Env. Microbiol. 62: 3210-3219).

Other continuous configurations based on two- or multi-stage vessels have been proposed in an attempt to separate and control the biphasic fermentation, but none have proved successful due to difficulties in controlling the flow rates and corresponding dilution rates to maximise solvent productivity (see below). Mixed cell populations of acidogenic and solventogenic cells quickly build up in both the first and second stage, providing oscillations in growth and solvent formation. For free cell suspensions if flow rates are not controlled, this typically results in cultures that wash out if growth slows or perform sub-optimally at low flow rates. In addition, cultures tend to degenerate quickly losing the ability to produce solvents (Woolley and Norris (1990) J. Appl. Bacteriol. 69: 718-728; Jones and Woods, (1986) supra; Kashket and Cao (1995), FEMS Microbiol. Rev., 17, 307-315; Afschar (1990) DE 3905624 A1). Afschar (1990) proposed a two stage molasses fermentation process for the production of butanol and acetone, which is characterized by a chemostat with substrate limitation at the first stage to produce cells. A two-stage continuous cultivation for clostridia was also proposed by Mutschlechner et al. (J. Mol. Microbiol. Biotechnol. (2000) 2(1):101-105). In this process, the system was designed to mimic the two phases of batch culture growth by using a first stage to grow the cells acidogenically as quickly as possible and then transferring cells to the second stage at the 'acid break point'. The second vessel is larger to provide sufficient residence time to complete solvent production. In both of these examples, the flow rates into the first and second stage were kept constant and not regulated in response to any growth related signals such as changes in pH or cell density.

Two-stage continuous cultures have also been described with immobilized biomass or cell-retention (e.g. Maddox et al. (1993), supra; Gapes et al. (1996), supra). These authors used a fixed dilution rate and describe immobilisation methods to retain the microbes in the reactor and to prevent them from washing out. These cultures can be run at high dilution rates and productivities but the final solvent concentrations tend to be too low for cost-effective recovery. Also, in both examples, solvent titres and productivity oscillated widely. The main drawback with immobilisation is the expense and difficulty to scale. Operation over prolonged periods and/or use of feedstocks with particulates is problematical due to blockages and fouling of the support matrices. In addition, these systems are prone to contamination and difficult to keep sterile.

A sequential fermentation process has also been commercialized in China wherein a continual or sequential batch process is used with eight fermentors linked together. The first two vessels (vessels 1 and 2) are biomass generators and are continuously re-seeded with fresh culture every 24 hours (via a conventional seed train). The biomass generators, once seeded, are fed continuously with substrate (feedstock) and, when full, the liquid flow goes forward to vessels 3 and 4 (which work in parallel). These two vessels then feed the rest of the fermentation train, which consists of a sequential series of connected vessels (usually four) giving a total process residence time of 72 h in the eight fermentation vessels. This complicated process has been designed around the biphasic nature (& limitations) associated with *C. acetobutylicum* which generally requires continual re-seeding to avoid microbe degeneration (due to loss of solvent plasmid). This process is controlled manually, with very little scope to respond quickly to process fluctuations. The continual Chinese process is described in Ni & Sun (2009), Appl. Microbiol. Biotechnol., 83, 415-423.

To date, fermentation process technology has been developed for biphasic solvent producing clostridia. The metabolism is characterised by rapid growth and acid formation and then a transition during which growth slows, acids are re-assimilated and solvent production starts. This results in relatively long fermentation times.

There remains a need, however, to provide a process which provides early onset of solvents, shorter fermentation times and, if fed continuously, continuous or extended solvent production for periods in excess of 50 hours.

It is one aim of the invention, therefore, to provide a fed batch or continuous fermentation process which optionally integrates solvent removal with cell and water recycling operations and which enables high solvent productivity to be maintained for periods in excess of 50 hours. The inventors have found that such an integrated system can be used to convert high concentrations of sugar or other carbon feeds into solvents (acetone, butanol and ethanol) at high yield over a prolonged period of time with minimal substrate inhibition.

This invention is based on the surprising discovery that certain solventogenic clostridia are in fact not biphasic; they are monophasic. In batch fermentations monophasic solvent production is characterised by simultaneous growth and solvent production with no obvious switch or change in metabolism from acid to solvent production during the major growth phase. Indeed, acids and solvents are produced simultaneously and acids do not tend to accumulate in the culture media. In these clostridia, it is not necessary to wait for the second phase before solvents are produced. For such clostridia, growth and solvent production can occur in a single vessel. Solvent production can be controlled by monitoring cell growth or a growth-related feature (e.g. production of gas, sugar utilisation or production of acid) and optimising the conditions for cell growth, thus obtaining high cell densities and solvent titres. This approach contrasts with previous approaches wherein the culture conditions have been optimized for either growth in the acidogenic phase or solvent production in the solventogenic second phase.

The batch fermentation profiles for monophasic and biphasic solventogenic clostridia are shown in FIGS. 2 and 3.

In one embodiment, therefore, the invention provides a single-stage process for the production of a solvent, the process comprising the steps:
(a) culturing monophasic solventogenic clostridial cells in a liquid culture medium in a culture vessel;
(b) monitoring cell growth of the monophasic solventogenic clostridial cells in the culture vessel;
(c) continuously or semi-continuously introducing fresh culture media and/or nutrients into the culture vessel;
(d) continuously or semi-continuously removing a stream or portion of liquid culture medium comprising solvent(s) from the culture vessel and passing said liquid culture medium to a solvent remover;
(e) maintaining or increasing cell density within the culture vessel;

wherein cell growth in the culture vessel is regulated and/or optimized by controlling:
(i) the amount or rate of fresh culture medium or nutrients which are introduced into the culture vessel, and/or
(ii) the amount or rate of liquid culture medium comprising solvent(s) which is removed from the culture vessel.

Preferably, the monophasic *clostridium*:
i) naturally displays simultaneous growth and solvent production during the major growth phase of batch fermentations;
ii) has been chemically mutated to produce solvents during growth; or
iii) has been genetically modified to produce solvents during growth.

Preferably, the *clostridium* is a monophasic *C. saccharoperbutylacetonicum*.

Most preferably, the *clostridium* is a monophasic *Clostridium saccharoperbutylacetonicum* N1 strain, e.g. N1-4(HMT) or N1-504.

Preferably, step (b) comprises monitoring cell growth by one or more of:
(i) monitoring production of one or more gases (e.g. hydrogen and/or $CO_2$);
(ii) monitoring production of one or more acids;
(iii) monitoring the pH of the culture medium;
(iv) monitoring the utilisation of sugar;
(v) monitoring cell density; and
(vi) monitoring the production of one or more solvents.

Preferably, step (d) comprises continuously or semi-continuously removing a stream or portion of the liquid culture medium from the culture vessel and passing the stream/portion via a cell separator to a solvent remover, wherein:
(i) cells are removed from the liquid culture medium in the cell separator and the cells are returned to the culture vessel (optionally via a cell seeder), and
(ii) wherein solvent is removed from the liquid culture medium in the solvent remover and the residual liquid culture medium is returned to the culture vessel.

Preferably, the cell density is maintained or increased within the culture vessel by:
(i) recycling cells which are removed from the liquid culture medium comprising solvent(s) back to the culture vessel; and/or
(ii) continuously or semi-continuously feeding cells from a cell seeder into the culture vessel; and/or
(iii) immobilisation of some or all of the cells within the culture vessel.

The process of the invention may be operated in any suitable manner. For example, it may be operated as a fed-batch process or any form of continuous process or perfusion process; or a mixture of these types of processes.

In some embodiments, the process is operated in fed-batch mode. In this embodiment, the microorganism is cultured under desired growth conditions in a batch mode for a suitable time, e.g. about 20 hours until approximately half the sugars are consumed (e.g. 25-30 g/L). The cells of the microorganism multiply and produce both acids and solvents. The initial volume of the first batch stage of the process should preferably be about 70% (e.g. 65%-75%) of the total working volume in the vessel and contain enough sugar (e.g. 55-65 g/L) and nutrients to sustain growth and good solvent yields (e.g. greater than 0.3 g solvents/g sugar). The fermentor is fed with a concentrated sugar solution and nutrients in a volume that equates to about 30% (e.g. 25%-35%) of the culture vessel's working capacity and is fed at a rate designed to last for a finite number of hours (e.g.

between 10-75 hours) The microorganisms are maintained under conditions that are suitable for them to grow optimally and produce solvents (e.g. temperature, pH, redox).

The process of the invention is preferably operated under continuous culture conditions. As used herein, the term "continuous culture conditions" refers to a process wherein the culture of microorganisms in the culture vessel is capable of being maintained with a continuous or substantially continuous flow of feed (nutrients) in steady state conditions (defined by high sugar uptake rates and solvent productivity) for prolonged periods of time (e.g. >75 hours). Under this scenario, some bleed may be required to maintain a constant volume in the culture vessel.

Solventogenic clostridia are bacteria that are capable of producing solvents such as acetone, butanol and ethanol. Typically, acids are first produced and then re-assimilated into solvents in a biphasic fermentation.

The process of the invention is a single stage process. As used herein, the term "single stage" means that both acid(s) and solvent(s) are produced together in the same culture vessel. This may be contrasted with a two-stage process wherein acids are produced in a first growth stage and solvents are subsequently produced in a second stage, typically performed in two culture vessels.

In most solventogenic clostridia (e.g. *Clostridium acetobutylicum*), fermentation is biphasic: the first phase is characterised by cell growth, acid production and a fall in culture pH; in the second phase, the acids are converted to solvents and the culture pH increases. The switch in metabolism is triggered by the acid concentration in the fermentation broth and/or low culture pH values.

The invention, however, relates to monophasic clostridia. As used herein, the term "monophasic clostridia" means that the clostridia do not have distinct acid- and solvent-producing phases. Monophasic solvent production is characterised by simultaneous growth and solvent production; and with no obvious switch or change in metabolism. Acids do not tend to accumulate in the culture media.

Preferably, the microorganism is a monophasic solventogenic *clostridium*.

Preferably the microorganism is a biphasic *clostridium* that has been converted to display monophasic fermentation either by chemical mutagenesis or specific genetic modification or a combination of both.

More preferably, the microorganism naturally displays monophasic metabolism without the need for modification.

More preferably, the *clostridium* is a monophasic *Clostridium saccharoperbutylacetonicum*.

Most preferably, the *clostridium* is a monophasic *C. saccharoperbutylacetonicum* N1 strain, e.g. N1-4(HMT) or N1-504, or a variant or derivative thereof. Such variants/derivatives will also be monophasic solventogenic clostridia. Preferably, the variants/derivatives produce the same or more acetone, ethanol and/or butanol compared to the clostridia from which they are derived, under equivalent conditions.

Such variants may be produced, for example, by random mutagenesis or by recombinant methods. Recombinant methods include insertional inactivation of genes through use of Type II introns, e.g. Targetron (Sigma) and Clostron (e.g. WO 2007/148091), and integration of new genes through use of 'allele coupled exchange' (ACE, e.g. WO 2009/101400). Random mutagenesis techniques could also be used, as previously demonstrated for generating a more acetate-tolerant strain (Yang, S., Land, M. L., Klingeman, D. M., Pelletier, D. A., Lu, T. Y., Martin, S. L., Guo, H. B., Smith, J. C., & Brown, S. D. (2010). Paradigm for industrial strain improvement identifies sodium acetate tolerance loci in *Zymomonas mobilis* and *Saccharomyces cerevisiae*. Proc Natl Acad Sci USA., 107(23), 10395-400. 2010.), for generating a more ethanol-tolerant strain (Shao, X., Raman, B., Zhu, M., Mielenz, J. R., Brown, S. D., Guss, A. M., & Lynd, L. R. (2011). Mutant selection and phenotypic and genetic characterization of ethanol-tolerant strains of *Clostridium thermocellum*. Appl Microbiol Biotechnol. 92(3), 641-52. 2011. Also: Brown, S. D., Guss, A. M., Karpinets, T. V., Parks, J. M., Smolin, N., Yang, S., Land, M. L., Klingeman, D. M., Bhandiwad, A., Rodriquez, M. Jr., Raman, B., Shao, X., Mielenz, J. R., Smith, J. C., Keller, M., & Lynd, L. R. (2011). Mutant alcohol dehydrogenase leads to improved ethanol tolerance in *Clostridium thermocellum*. Proc Natl Acad Sci USA., 108(33), 13752-7. 2011.) and for generating a more amylolytic strain (Annous, B. A., & Blaschek, H. P. (1991). Isolation and characterization of *Clostridium acetobutylicum* mutants with enhanced amylolytic activity. Appl. Environ. Microbiol., 57(9), 2544-8. 1991.)

Such variants may be tested by screening them in small-scale fermentations, i.e. looking for variants that retain monophasic behaviour and produce the same or more acetone, ethanol and/or butanol compared to the clostridia from which they are derived, under equivalent conditions.

*C. saccharoperbutylacetonicum* strain N1-4(HMT) may be obtained from ATCC deposit number 27021. *C. saccharoperbutylacetonicum* strain N1-504 may be obtained from ATCC deposit number 27022.

In some embodiments of the invention, the *clostridium* is not *C. saccharoperbutylacetonicum* strain N1-4. *C. saccharoperbutylacetonicum* strain N1-4 was previously available as ATCC deposit number 13564. This deposit is, however, no longer available.

The term "acid-producing" or "acidogenic" refers to the ability of the *clostridium* to convert a substrate based on sugars and/or starches into RCOOH (wherein R is as defined below), for example into acetate and/or butyrate.

The term "solvent-producing" or "solventogenic" refers to the ability of the *clostridium* to convert a substrate based on sugars and/or starches into a solvent, preferably into one or more of acetone, ethanol and/or butanol.

As used herein, the term "solvent" or "solvents" refers to low boiling point organic solvents or their azeotropes which are capable of being produced by solventogenic microorganisms in a liquid fermentation medium. Examples of such solvents include alcohols of formula R—OH, wherein R is an aliphatic C1-C8 alkyl group or an aliphatic C2-C8 alkenyl group. The R group may be branched or linear. Preferably, it is linear. The R group may be saturated or unsaturated. Preferably it is saturated.

Preferred examples of alcohols of formula R—OH include methanol, ethanol, 2-methyl-propan-1-ol, 1,3-propanediol, 1-butanol, 2-butanol, 2-methyl propan-2-ol, pentanol, hexanol, heptanol and octanol. A further example of a solvent has a formula R—CO including acetone $((CH_3)_2CO)$.

Preferably, the solvents comprise ABE solvents, i.e. acetone, 1-butanol and ethanol. Most preferably, the solvents comprise 1-butanol or substantially 1-butanol.

The *clostridium* may be an aerobic or an anaerobic microorganism. Preferably it is an anaerobic or aero-tolerant *clostridium*. Most preferably, it is an aero-tolerant *clostridium*.

In some embodiments, the culture vessel may be inoculated with no special precautions taken to exclude oxygen or no anaerobic purge. Furthermore, the culture vessel may be operated with air (of normal atmosphere composition) in the head-space above the culture medium.

In some embodiments of the invention, the process is performed under conditions which are not oxygen-free.

The acid- and solvent-producing clostridia which are used in the culture vessel may be from a single strain or from a co-culture, preferably from a single strain.

In some embodiments, the clostridia are acid-tolerant. The clostridia can preferably tolerate high concentrations of COOH. In this context, high concentrations of COOH may mean up to 15 g/L acetic acid, and/or up to 10 g/L lactic acid and/or up to 6 g/L formic acid.

In some embodiments, some or all of the clostridial cells may be immobilised in the culture vessel. In other embodiments, the clostridial cells are non-immobilised or are in free suspension.

The culture vessel may be any form of culture vessel which is suitable for culturing the clostridial cells in the process of the invention. Preferred types of culture vessel include conventional stirred bioreactors.

As used herein, the term "culture vessel" includes two or more culture vessels which may or may not be linked in fluid communication. Any multiple culture vessels may be linked in parallel or in series.

In the context of the invention, however, the acid(s) and solvent(s) are both produced together (i.e. in a mixture) in a single culture vessel. It is not the case that one or more acids are produced in a first culture vessel and they are then converted to one or more solvents in a second culture vessel.

Suitable culture media are well known in the art. These will be selected according to the *clostridium* which is being used. Generally, the culture medium will be an aqueous medium.

In embodiments of the invention which comprise a fed batch process, the fermentation proceeds in batch mode for approximately 20 hours with approximately 70% of the reactor volume filled. The medium should contain enough sugar and nutrients for the microorganisms to grow optimally and to produce acids and some solvent(s).

In other embodiments, it is possible initially to fill, and inoculate only about 10% of the reactor working volume. The remaining about 60% may be filled during cell growth.

The medium for the fed-batch process may be a nutrient feed containing higher sugar and/or nutrient concentrations than those present in the culture vessel during the batch stage. Typical concentrations of the sugar on the feed may vary between 250 g·L$^{-1}$ and 450 g·L$^{-1}$. This may be fed at a constant flow rate or controlled by a feedback system based on either cell growth (or a related feature), or sugar or solvent levels in the culture vessel. In other embodiments, the addition of extra nutrient media may commence using an independent trigger than that of the solvent extraction; this may be, for example, when the sugar concentration has dropped between a defined level (e.g. below 30 g/L) or when a slow-down in growth rate is detected.

The feed rate of the additional sugar solution should preferably keep pace with the uptake rate of the culture. This may, for example, be about 2-5 g·L$^{-1}$·h$^{-1}$ through the feed stage in order to maintain a steady sugar concentration in the culture vessel (e.g. in the range of 5-30 g·L$^{-1}$).

The clostridia in the culture vessel are maintained under conditions which are suitable for them to produce acids and solvents. The conditions will include the provision of nutrient media comprising appropriate carbon sources, for example assimilable carbohydrates.

Examples of assimilable carbohydrates are sugars such as C5 and C6 monomers, C5 and C6 sugar dimers, sugar oligomers and sugar polymers. Preferred sugars are arabinose, xylose, mannose, fructose, glucose, galactose, sucrose, lactose, maltose, cellobiose. Preferred polymers are starch, xylan, pectin, fructan, cellulose and mannitol. Another suitable carbon source is glycerine.

Preferably, sugars are hydrolysates derived from lignocellulosic feedstocks such as agricultural residues (corn & sugar), woody residues, energy crops or municipal waste.

The carbohydrate may also be a glucose-based polysaccharide, e.g. a starch or a starch-based material. Most preferably, the carbohydrate is starch or a starch-based material, e.g. corn, corn starch, corn mash, potato, potato starch, potato mash, potato peeling, potato chips, cassava, cassava starch, cassava chips, sago, sago starch, dextrin or 'soluble starch', e.g. as sold by Fisher/Sigma.

In some embodiments, the invention allows the use of greater than 200 g/L sugar or other carbon feed with minimal substrate or solvent inhibition, whilst keeping yields of products greater than 30% on carbon-fed basis.

The pH of the culture vessel may be controlled through the automated addition of alkali from a separate alkali feed or from the addition of feed media that has a pH lower than the culture vessels (typically 1-2 pH units).

The pH of the culture vessel is preferably pH 5.5-7.0, more preferably pH 5.5-6.5.

The pH may also be controlled by a pH auxostat. Preferably, the pH-auxostat has a separate alkali feed and the pump is linked to the pump controlling the media feed. The cell density in the culture vessel may be controlled by altering the ratio or relative speed of the alkali-feed and media-feed pumps.

The temperature will be selected as being one at which the microorganism grows best. For example, for mesophilic clostridia the temperature is preferably 30-37° C., more preferably 31-33° C., e.g. about 32° C.

In step (b), growth of the monophasic solventogenic clostridial cells in the culture vessel is monitored. This is done in order to obtain information which can be used to maintain good growth rates and high cell densities within the culture vessel by the addition of fresh culture media or nutrients and/or removal of solvents.

Although the cell growth of the clostridia which are in the culture vessel is monitored, the actual monitoring may or may not be done in the culture vessel, e.g. the monitoring may be done externally or on a sample which is removed from the culture vessel.

Preferably, step (b) comprises monitoring cell growth by one or more of:
  (i) monitoring production of one or more gases (e.g. hydrogen and/or $CO_2$);
  (ii) monitoring production of one or more acids;
  (iii) monitoring the pH of the culture medium;
  (iv) monitoring the utilisation of sugar;
  (v) monitoring cell density; and
  (vi) monitoring the production of one or more solvents.

During the process of the invention, one or more gases may be produced by the clostridia. These gases may include hydrogen and/or carbon dioxide.

The total amount of gas may be monitored using a flow meter and individual gases may be quantified using specific gas analysers.

The ratio of gases may also be monitored and used to control growth and solvent production by adjusting the addition of culture media, nutrients and/or removal rate of solvents.

The clostridia convert substrates based on sugars and/or starches into acids (e.g. RCOOH, wherein R is as defined above). Exemplary acids include acetate and/or butyrate. The acid concentration may be monitored by gas chromatography (GC).

The production of these acids may also be monitored by a change in culture pH. In this case, the monitoring apparatus may be a pH meter.

Cell density may be monitored by optical means, for example determining the optical density (OD) at 600 nm.

In other embodiments, a change in cell density may be linked to a change in the rate of fresh media/nutrient feed or removal of culture media comprising solvent(s), e.g. by using a turbidostat.

The production of one or more solvents (e.g. ethanol, butanol, acetone) may be monitored by gas chromatography (GC) and/or high performance liquid chromatography (HPLC).

Preferably, the butanol concentration in the culture vessel should not exceed 10 g butanol $L^{-1}$.

The utilisation of one or more sugars (e.g. glucose, xylose, fructose, arabinose, sucrose, cellobiose, or others as appropriate depending on the feedstock) may be monitored by HPLC.

Preferably, the sugar concentration in the culture vessel should not exceed 30 g sugar $L^{-1}$.

Step (d) comprises continuously or semi-continuously removing a stream or portion of liquid culture medium comprising solvent(s) from the culture vessel and passing said liquid culture medium to a solvent remover. In the solvent remover, one or more solvents are preferably separated from the liquid culture medium, and optionally isolated.

Preferably, step (d) comprises continuously or semi-continuously removing a stream or portion of the liquid culture medium from the culture vessel and passing the stream/portion via a cell separator to a solvent remover, wherein:
(i) cells are removed from the liquid culture medium in the cell separator and the cells are returned to the culture vessel (optionally via a cell seeder), and
(ii) wherein solvent is removed from the liquid culture medium in the solvent remover and the residual liquid culture medium is returned to the culture vessel.

The liquid culture medium from the culture vessel may be passed directly or indirectly to the cell separator.

The residual liquid culture medium may be passed directly or indirectly to the culture vessel, e.g. it may be stored temporarily, e.g. in a reservoir.

In order to reduce loss of cells from the culture vessel, a cell separator may be positioned upstream of the solvent remover. In the cell separator, all or a substantial portion of the cells are removed from the stream or portion of the liquid culture medium which is passed through the cell separator. For example, the cell separator may remove at least 50%, preferably at least 70%, and most preferably at least 80% or at least 90% of the cells from the liquid culture medium which is passed through the cell separator.

Examples of cell separators include hollow fibre separators, membrane separators and centrifugal separators.

After separation from the liquid culture medium, the cells are returned to the culture vessel (preferably with some liquid culture medium), optionally via a cell seeder.

The remaining liquid is then passed to the solvent remover.

In step (d)(ii), solvent is removed from the liquid culture medium by a solvent remover and the residual liquid culture medium (i.e. the liquid culture medium from which some or all solvents have been removed) is returned to the culture vessel.

The liquid culture medium which is removed from the culture vessel will be enriched in one or more solvents which have been produced by the solventogenic clostridia.

Preferably, liquid culture medium starts to be removed from the culture vessel once the solvent(s) produced in the culture vessel reach a defined concentration point (e.g. 8-10 g butanol $L^{-1}$ liquid culture media).

The liquid culture medium should preferably be passed to the solvent remover at a rate which maintains the solvent concentration in the liquid culture medium below the desired solvent concentration point. This concentration point may, for example, be the toxicity threshold for the specific solventogenic *clostridium* used.

Generally, the solvent(s) will be recovered from the liquid culture medium (fermentation broth) by one or more of liquid-liquid extraction, ionic-liquid extraction, gas stripping, vacuum evaporation, atmospheric or vacuum distillation, pervaporation, ion-exchange adsorption, counter-current solvent extraction and/or distillation. Alternatively, hydrophobic membranes may be used, e.g. with air flux or inert gas carrier or vacuum (pervaporation) to aid the separation (preferably in a continuous process).

Preferably, the solvent(s) will be recovered from the liquid culture medium by atmospheric or vacuum distillation, pervaporation, liquid-liquid extraction and/or gas stripping.

Preferably, the solvent extraction is performed continuously.

In some embodiments of the invention, solvent may be produced at a rate of at least 0.8 g·$L^{-1}$·$h^{-1}$ for periods in excess of 60 hours or 0.6 g·$L^{-1}$·$h^-$ for over 100 hours.

In some more preferable embodiments, solvent extraction is via continuous atmospheric or vacuum distillation.

Once the solvents are removed from the liquid culture medium, some or all of the residual liquid culture medium is returned to the culture vessel. This maximizes utilization of nutrients from the liquid culture medium and minimises water loss.

The invention also relates to a solvent which is obtained by a process of the invention.

In step (e), the cell density is preferably maintained or increased within the culture vessel by one or more of:
(i) recycling cells which are removed from the liquid culture medium comprising solvent(s) back to the culture vessel;
(ii) continuously or semi-continuously feeding cells from a cell seeder into the culture vessel; and
(iii) immobilising some or all of the cells within the culture vessel.

In step (e)(ii), cells are continuously or semi-continuously fed from a cell seeder into the culture vessel.

In the simplest version of the fermentation process a single batch seed of 5-10% v/v can be used to inoculate the fermentation at the beginning of the fermentation; However it is possible also to use multiple batch inoculations of 5-10% v/v at various time intervals during the fermentation in order to maintain high cell densities and solvent productivities. Alternatively, continuous culture can be used to provide a continuous supply of fresh cells to the production fermentor. The preferred embodiment is a pH-auxostat that is fed from the still bottoms from distillation and self-regulated using a set pH value to control the addition of feed and/or fresh nutrients and sugars.

In step (e)(iii), some or all of the clostridial cells may be immobilized in the culture vessel.

The cells could be immobilized by active immobilization techniques, whereby free suspended cells are immobilized by covalent attachment to surfaces, cross-linking of cells to surfaces, entrapment within gels or membrane confinement; or by passive immobilization, exploiting the natural tendency of cells to adhere to solid porous surfaces due to electrostatic interactions or by their ability to form films or aggregates around or within a support material.

The preferred methods for immobilizing clostridia in this application are:
  (i) entrapment of cells within a gel matrix made of naturally occurring polymers (eg alginates, kappa-carrageenan, collagen, gelatine, cellulose, etc.) or synthetic gels (polyacrylamide, polymethacrylamide, photo-cross-linkable resin pre-polymers, urethane pre-polymers, polyethyleneglycol and polyvinyl alcohol, etc.)
  (ii) membrane confinement of cells by immobilization behind a barrier. The barriers can be droplets of cell-water suspensions emulsified in organic solvents or semi-permeable membranes.

In the process of the invention, cell growth (or the rate of cell growth) in the culture vessel is regulated by controlling:
  (i) the amount or rate of fresh culture medium or nutrients which are introduced into the culture vessel, and/or
  (ii) the amount or rate of liquid culture medium comprising solvent(s) which is removed from the culture vessel.

The aim of the process of the invention is to maintain cell growth and optimize cell density within the culture vessel with a view to maximizing sugar utilization and solvent production.

By monitoring cell growth of the clostridia in the culture vessel, sub-optimal growth may be detected. Optimal growth may then be sought or obtained by the introduction of fresh culture media or nutrients into the culture vessel and/or the removal of some liquid culture media comprising inhibiting solvents.

Preferably, therefore, the growth of cells in the culture vessel is maintained at an optimal level.

In other embodiments, if suboptimal growth of cells is detected, fresh media or nutrients are introduced into the culture vessel and/or liquid media comprising solvents are removed from the culture vessel.

In yet other embodiments, the monitored level of cell growth is compared to a reference level and fresh media or nutrients are introduced into the culture vessel and/or liquid media comprising solvents are removed from the culture vessel if the monitored level is lower than the reference level.

The invention also provides a system for the production of a solvent, the system (e.g. as shown in FIG. 1) comprising:
  (i) a culture vessel for culturing a solventogenic *clostridium* in a liquid culture medium;
  (ii) monitoring apparatus for monitoring growth of cells in the culture vessel;
  (iiia) a cell seeder in fluid communication with the culture vessel and arranged to provide clostridial cells to the culture vessel, and/or (iiib) a cell separator in fluid communication with the culture vessel and arranged to receive liquid culture medium from the culture vessel and to separate solventogenic clostridial cells from the liquid culture medium and further arranged to return separated cells to the culture vessel;
  (iv) a solvent remover in fluid communication with the culture vessel and arranged to receive liquid culture medium, from which cells optionally have been removed by the cell separator further arranged to remove one or more solvents from liquid culture medium, and further arranged to return residual liquid culture medium to the culture vessel;
  (v) one or more flow regulators in fluid communication with the culture vessel for controlling the rate or amount of fresh culture media to be introduced into the culture vessel and/or the rate or amount of liquid culture medium to be passed to the cell separator;
  (vi) one or more controllers for controlling the one or more flow regulators depending on the input received from the monitoring apparatus.

The system may optionally also comprise one or more of the following:
  (vii) a beer still where the culture medium at the end of process is led to remove the bulk of the water from the solvents, e.g. through azeotropic distillation;
  (viii) one or more rectifying columns to purify the solvents to desired product specifications;
  (ix) stillage treatment to lower the COD/BOD (chemical oxygen demand/biochemical oxygen demand), optionally to also recover energy from the final culture medium with anaerobic fermentation or similar; and
  (x) one or more reservoirs of sugar solution and/or nutrients.

In some embodiments of the invention, the culture vessel comprises monophasic solventogenic clostridia in a liquid culture medium.

The system may additionally comprise a vessel which contains or is adapted to contain an alkali; and/or a vessel which contains or is adapted to contain fresh culture medium (nutrients). These latter vessels may be in liquid communication with the first culture vessel.

The means for liquid communication preferably comprises a pipe.

The system may additionally comprise one or more additional solvent removers (e.g. one or more rectifying columns, one or more beer stills, etc.) in fluid communication with the culture vessel and arranged to remove solvent from liquid culture medium which is removed from the culture vessel.

All of the features of the invention which are discussed above in the context of the process of the invention apply equally to the above system, *mutatis mutandis*.

EXAMPLES

Figure 1:
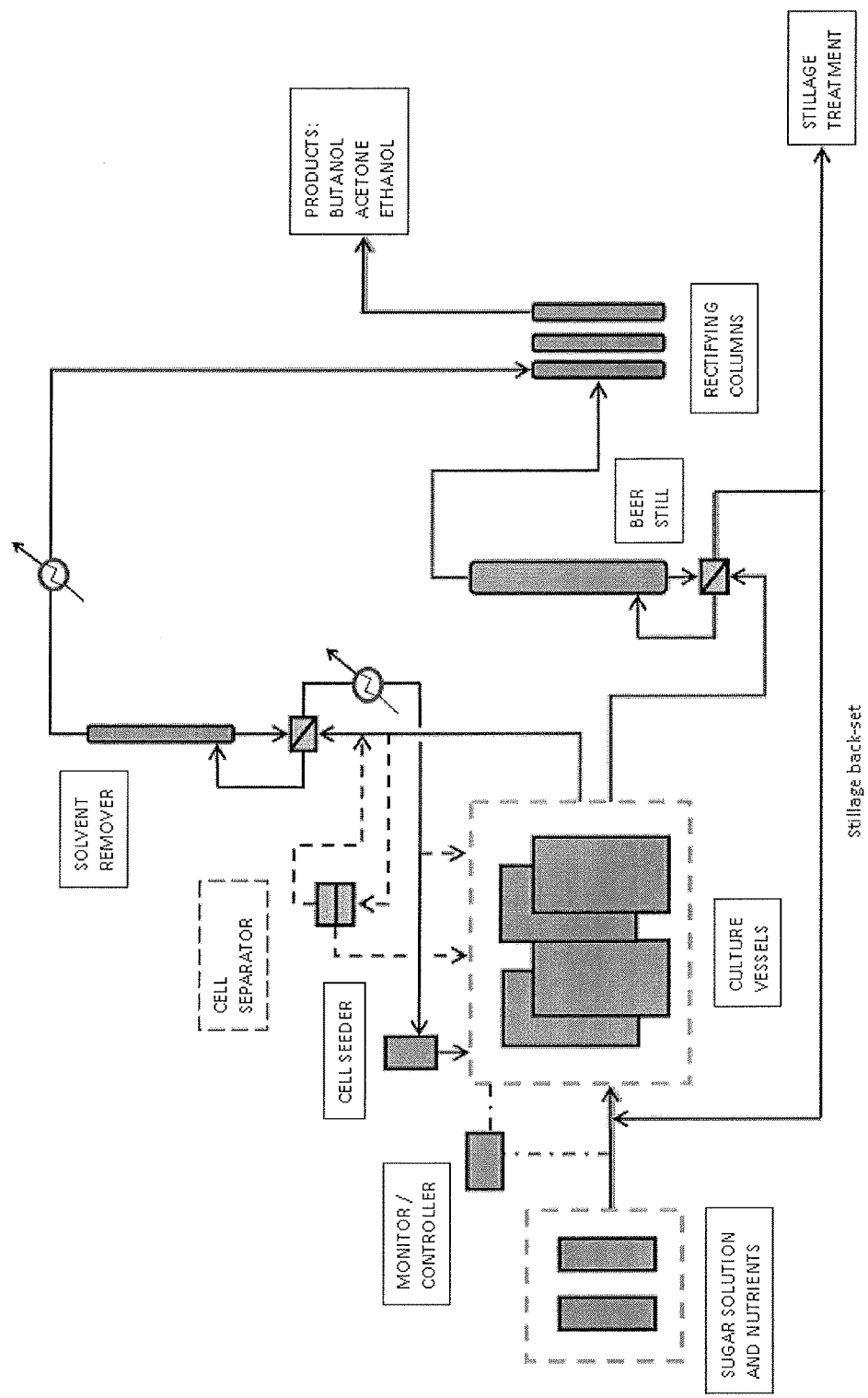
FIG. 1 shows an example of the integrated fed batch process concept of the invention.

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

In the lab scale (1 L) examples, gas-stripping is used to maintain a low level of solvents in the main fermentor. However in the pilot scale (140 L) examples (and the preferred commercial method), solvent removal is performed using atmospheric distillation with nutrient and water recycle to the main fermentor.

Comparative Example 1: Batch Fermentation with a Biphasic Solventogenic *Clostridium*

Objective:

To demonstrate the biphasic batch fermentation profile obtained using classical biphasic solventogenic clostridia.

Materials and Methods

Bacterial Strain

A solventogenic *Clostridium beijerinckii* strain BAS/B2 (CSC/NCP collection 15/06/1945) was cultured on a standard anaerobic culture medium such as reinforced clostridial medium (RCM—as in table 1) in 100 mL serum bottles under anaerobic conditions at 32±1° C. for 16-18 h.

TABLE 1

| RCM semi-solid medium composition in $g \cdot L^{-1}$ | |
|---|---|
| Yeast extract | 3.0 |
| Lab-Lemco powder | 10.0 |
| Peptone | 10.0 |
| Glucose | 5.0 |
| Soluble starch | 1.0 |
| Sodium chloride | 5.0 |
| Sodium acetate | 3.0 |
| Cysteine hydrochloride | 0.5 |
| Agar | 0.5 |
| *pH | 6.8 ± 0.2 |

*Adjusted as required to meet performance standards, sterilised by autoclaving at 121° C.

Fermentation Medium

Molasses was the main carbon source for the fermentation medium. Experiments were carried out at an initial volume of 0.95 L with starting molasses sugar concentrations of 60 $g \cdot L^{-1}$ in the fermentation vessel and supplemented with 5 $g \cdot L^{-1}$ corn mash, 5 $g \cdot L^{-1}$ $CaCO_3$ and 2 $g \cdot L^{-1}$ $(NH_4)_2SO_4$. The initial pH was adjusted with NaOH 20% (w/v) to 6.7±0.2, thereafter the pH was not controlled. All mineral salts were laboratory grade (Fisher Scientific).

Culture Conditions

Fermentations were carried out in 1 L fermentors with initial working volumes of 0.95 L. The fermentors were equipped with gas exhaust, stirrers, sampling ports, pH and temperature probes. They were initiated by inoculation with 1% v/v seed culture of the final volume (1 L). The temperature was maintained at 32±3° C.

Analysis of Cell Growth, Products and Substrates

Growth was monitored at 600 nm using a Jenway 6300 spectrophotometer with cuvettes of 1 cm light path. Cultures were diluted if necessary so that the absorbance did not exceed 0.6 units.

Concentrations of acetate, butyrate, ethanol, acetone, and n-butanol were measured by applying the supernatant from centrifuged fermentation samples to gas chromatography on an Agilent Gas Chromatography system with a network sampler. The equipment was fitted with a capillary column (Agilent 19091F115E HP-FFAP) with a column temperature ramp from 80° C. up to 200° C. The carrier gas was $N_2$ with a flow rate between 0.8 mL·min$^{-1}$ and 1.3 mL·min$^{-1}$. The FID detector temperature (300° C.) was operated with a hydrogen flow at 50 mL·min$^{-1}$, air flow at 400 mL·min$^{-1}$ and make up flow ($N_2$) at 30 mL·min$^{-1}$. Isobutanol (99.5%) and isobutyric acid (99.5%) were used as internal standards, prepared at concentrations of 10 g·L$^{-1}$ each in HPLC grade water.

The sugar content of the fermentation samples was determined by high pressure liquid chromatography using a Dionex HPLC fitted with an ASI00 auto sampler and a Shodex RI 101 refractive index and UV detector. The separation column was Phenomonex Rezex-Pb$^{2+}$, operated at 85° C. HPLC grade water was used as the mobile phase at a flow rate of 0.6 mL/min. The sample injection volumes were 10 μl. The calibration curve was created by integrating the peak areas from chromatograms generated from solutions of sucrose, maltose, glucose or fructose (as appropriate, according to the particular sugar source used) at concentrations of 1, 5, 10, 15 and 20 g·L$^{-1}$ of sugar.

Results

Figure 2:
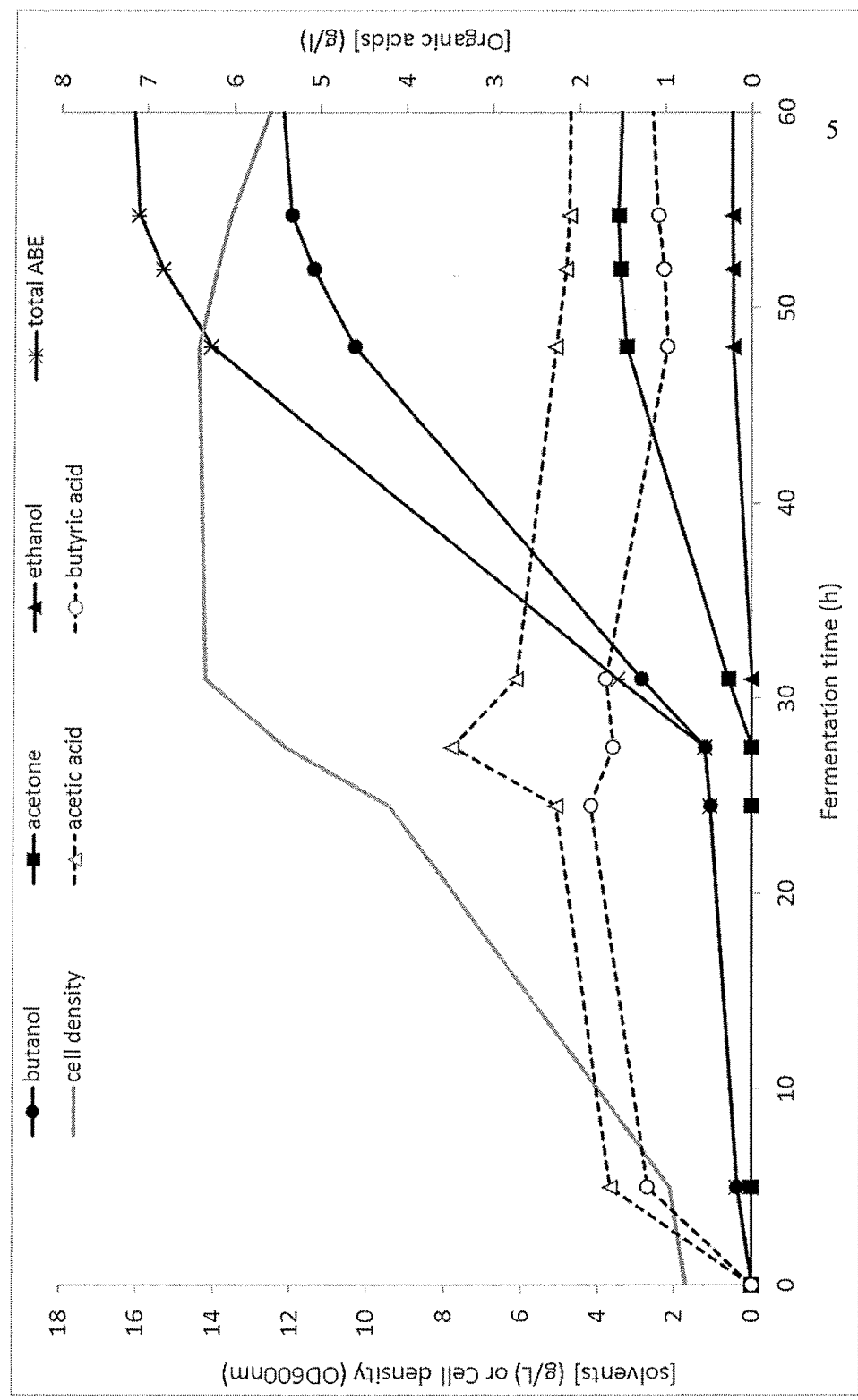
FIG. 2 is a batch fermentation profile for a biphasic solventogenic *clostridium*. The graph shows that solvent production starts when growth slows and the cells enter stationary phase. The fermentation time is relatively long. The final solvent titres are low and solvent productivity over the entire fermentation is therefore low (Example 1).

The results are shown in FIG. 2. The graph shows that solvent production starts when growth slows and the cells enter stationary phase. The fermentation time is relatively long (55 hours). The final solvent titres are low and solvent productivity over the entire fermentation is therefore low.

Comparative Example 2: Batch Fermentation with a Monophasic Solventogenic *Clostridium*

Objective:

To demonstrate the monophasic batch fermentation profile obtained using a monophasic solventogenic *clostridium*.

Materials and Methods

Bacterial Strain

A solventogenic *Clostridium saccharoperbutylacetonicum* strain N1-4(HMT) was cultured on a standard anaerobic culture medium such as reinforced clostridial medium (RCM—as in Table 1) in 100 mL serum bottles under anaerobic conditions at 32±1° C. for 16-18 h.

Fermentation Medium

As in example 1: Molasses was the main carbon source for the fermentation media. Experiments were carried at initial volume of 0.95 L with starting molasses sugar concentrations of 60 g·L$^{-1}$ in the fermentation vessel and supplemented with 5 g/L corn mash, 5 g/L CaCO$_3$ and 2 g/L $(NH_4)_2SO_4$. The initial pH was adjusted with NaOH 20% (w/v) to 6.7±0.2, thereafter the pH was not controlled.

Culture Conditions

Similar to Example 1: Fermentations were carried out in 1 L fermentors with initial working volumes of 0.95 L. The fermentors were equipped with gas exhaust, stirrers, sampling ports, pH and temperature sensors. They were initiated by inoculation with 1% v/v seed culture of the final volume (1 L). The temperature was maintained at 32±3° C.

Analysis of Products and Substrates

As described for Example 1.

Results

Figure 3:
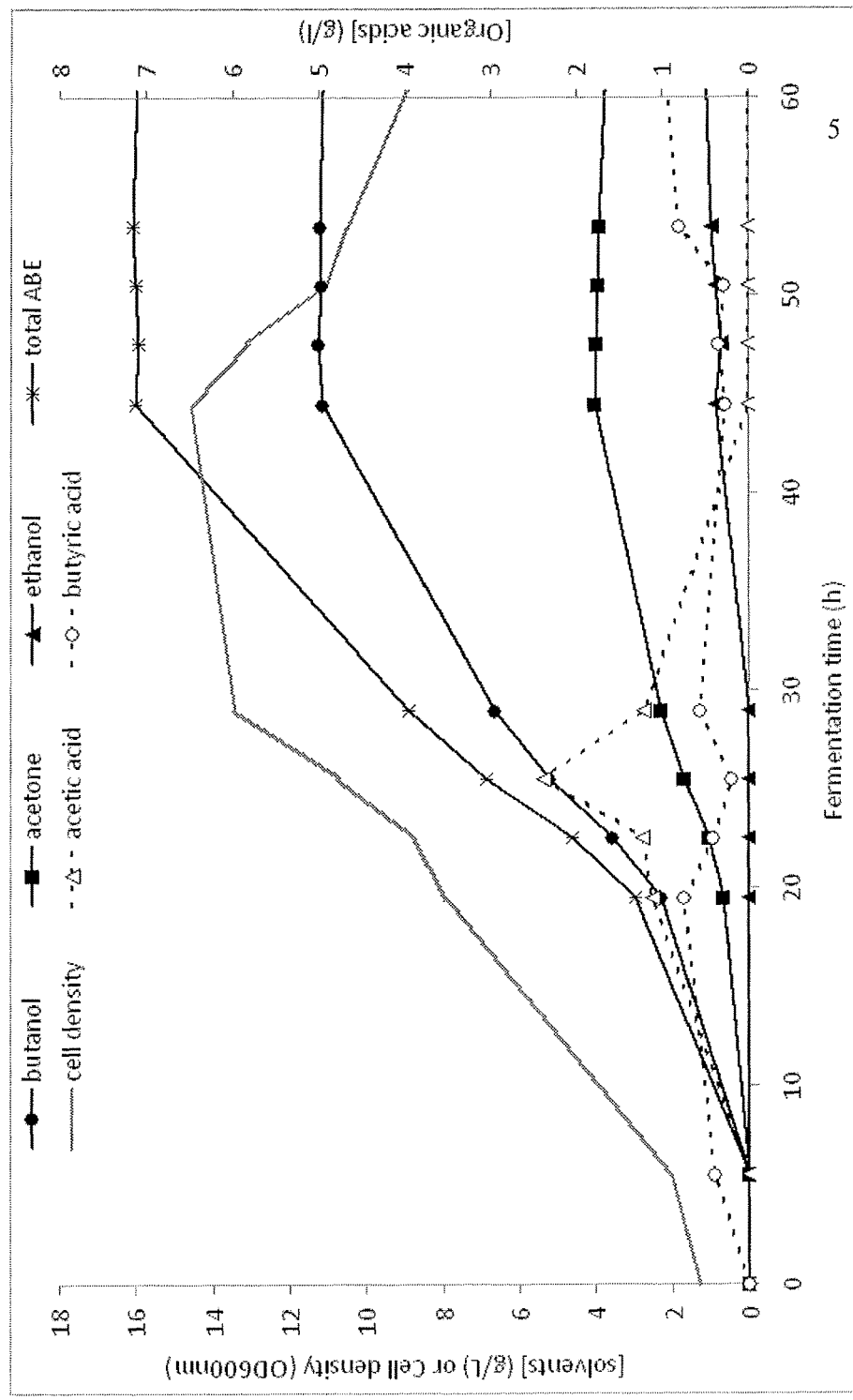
FIG. 3 is a batch fermentation profile for a monophasic solventogenic *clostridium*. The graph shows that solvent production occurs during growth and slows down when growth slows and the cells enter stationary phase. The fermentation time is reduced and solvent productivity over the entire fermentation is higher than in Example 1 (Example 2).

The results are shown in FIG. 3. The graph shows that solvent production occurs during growth and slows down when growth slows and the cells enter stationary phase. The fermentation time is reduced (45 hours) and solvent productivity over the entire fermentation is higher than in Example 1.

Comparative Example 3: Batch Fermentation with a Monophasic Solventogenic *Clostridium*

Objective:

To demonstrate the relationship between sugar utilisation and ABE production for a batch fermentation using a monophasic solventogenic *clostridium*.

Materials and Methods

Bacterial Strain

A solventogenic *Clostridium saccharoperbutylacetonicum* strain N1-4(HMT) was cultured as described in example 2.

Fermentation Medium

Similar to example 2: Molasses was the main carbon source for the fermentation media. Experiments were carried at an initial volume of 0.95 L with starting sugar concentrations of 55 g·L$^{-1}$ in the fermentation vessel and supplemented with 2.5 g·L$^{-1}$ yeast extract, 2.5 g·L$^{-1}$ tryptone, 0.025 g·L$^{-1}$ FeSO$_4$ and 0.5 g·L$^{-1}$ $(NH_4)_2SO_4$.

Culture Conditions

Similar to example 2: Fermentations were carried out in 1 L fermentors with initial working volumes of 0.8 L. The fermentors were equipped with gas exhaust, stirrers, sampling ports, pH and temperature sensors. They were initiated by inoculation with 7.5% v/v seed culture of the final volume (1 L). The temperature was maintained at 32±3° C. 20% w/v NaOH was used to adjust the initial pH to between 6 and 6.5, and when needed during the fermentation to maintain a pH set point of 5.0-5.5. All mineral salts were laboratory grade (Fisher Scientific).

Analysis of Products and Substrates

As described for Example 1.

Figure 4:
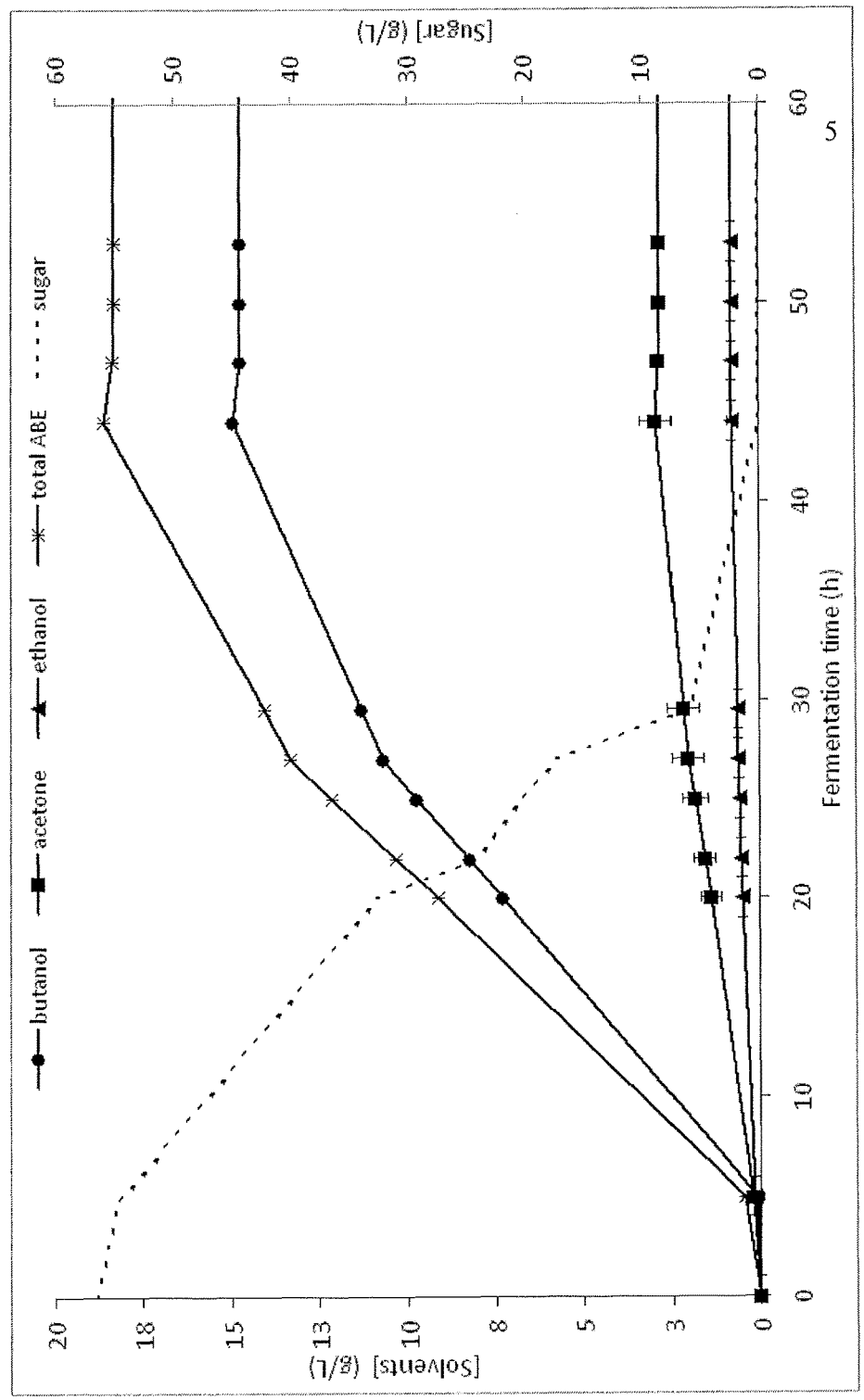
FIG. 4 is a batch fermentation profile with a monophasic solventogenic *clostridium*. The graph shows that sugars are utilised during solvent production and when sugars are exhausted solvent production stops. The fermentation time is relatively short (Example 3).

The results are shown in FIG. 4. The graph shows that sugars are utilised during solvent production and when sugars are exhausted solvent production stops. The fermentation time is relatively short (44 hours).

Example 4: Fed Batch Fermentation on Molasses

Objective:

To demonstrate a method to cultivate monophasic solventogenic clostridia at high production rates; using a fed batch system focused on the production of an exponentially growing cell population at or close to its maximum sugar uptake and solvent production rates for an extended time compared to traditional batch fermentation by keeping low solvent concentration in the broth (using gas stripping).

Figure 5:
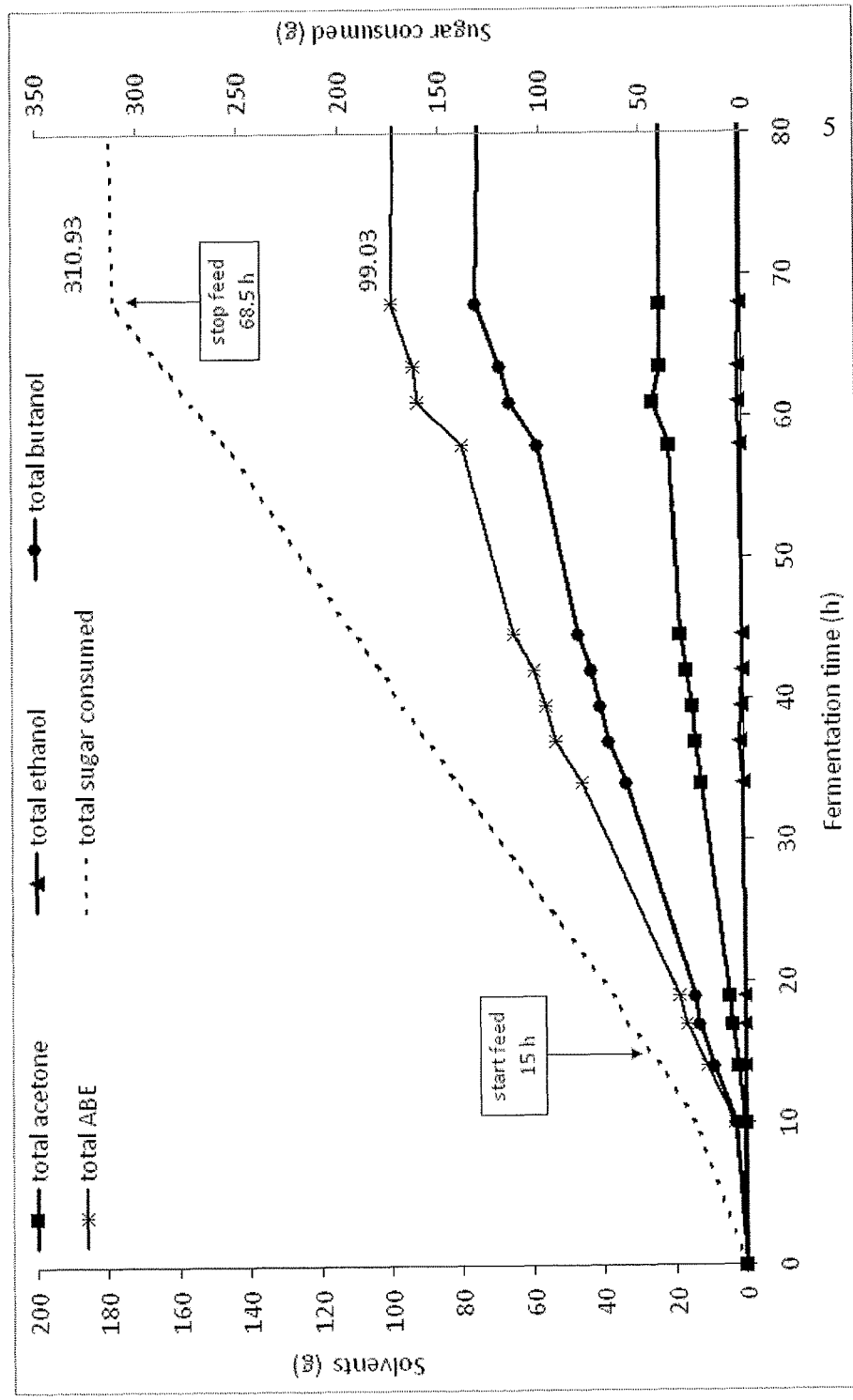
FIG. 5 is from a fed-batch fermentation with a monophasic solventogenic *clostridium*. Gas stripping is used to remove solvents and the sugar feed is molasses. The graph shows the accumulation in solvents (sum of solvents trapped outside and remaining within the fermentor) during the course of the fermentation. The final solvent titres obtained are much higher than those obtained in a conventional batch fermentation i.e. Example 3 (Example 4).
Figure 6:
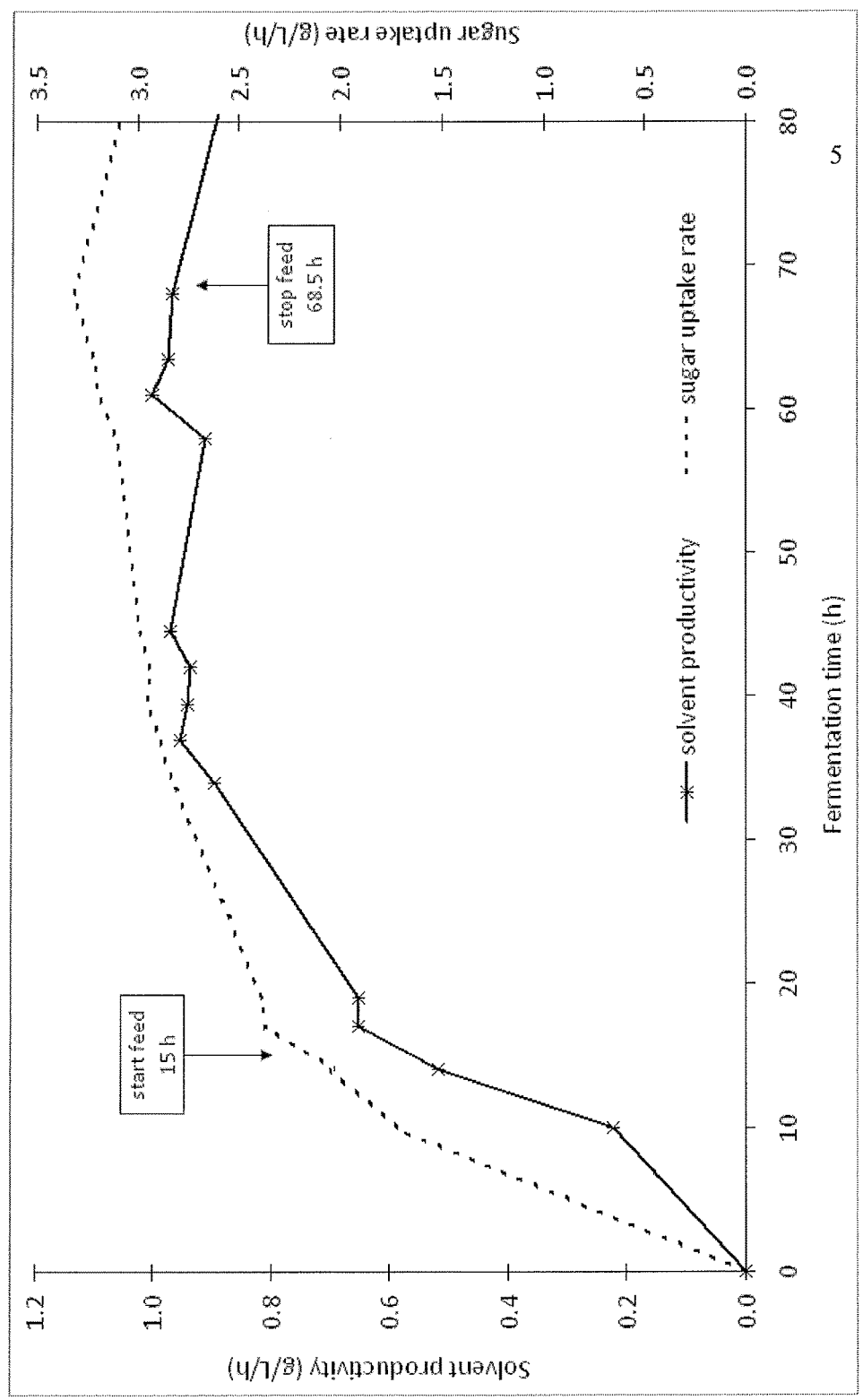
FIG. 6 is from a fed-batch fermentation with a monophasic solventogenic *clostridium*. Gas stripping is used to remove solvents and the sugar feed is molasses. The graph shows a correlation between solvent productivity and sugar uptake and that peak solvent productivity has been extended by adding additional sugar during the fermentation and by removing solvents as they are produced (Example 4).
Figure 7:
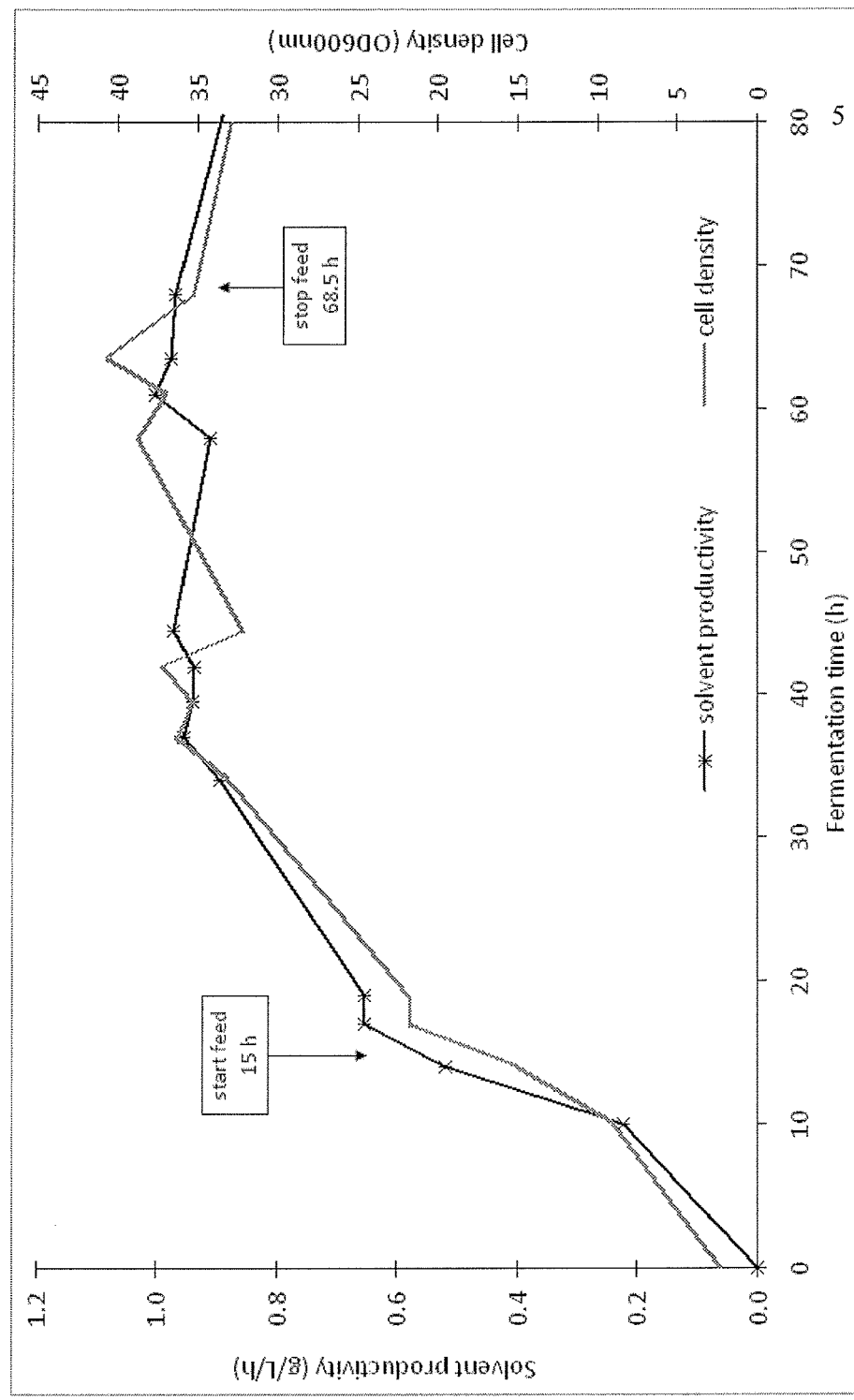
FIG. 7 is from a fed-batch fermentation with a monophasic solventogenic *clostridium*. Gas stripping is used to remove solvents and the sugar feed is molasses. The graph shows a direct correlation between cell growth and density (measured by optical density) and solvent productivity (Example 4).

Materials and Methods
Bacterial Strain
A solventogenic *Clostridium saccharoperbutylacetonicum* strain N1-4(HMT) was cultured as described in Example 2.
Fermentation Medium
Molasses was the main carbon source for the fermentation medium. Experiments were carried out at an initial volume of 1.5 L with starting sugar concentrations of 50 g·L$^{-1}$ in the fermentation vessel and supplemented 2.5 yeast extract, 2.5 g·L$^{-1}$ tryptone, 0.5 g·L$^{-1}$ (NH$_4$)$_2$ SO$_4$, 0.025 g·L$^{-1}$ FeSO$_4$, and 3 g·L$^{-1}$ CaCO$_3$. When needed, the pH was adjusted with 20% w/v of NaOH to a pH of 6.5 prior to sterilization. All mineral salts were laboratory grade (Fisher Scientific).
Feed Medium
500 mL of additional feed of glucose solution at a concentration of 350 g·L$^{-1}$, with nutrients 3.8 g·L$^{-1}$ yeast extract, 3.8 tryptone, 0.8 g·L$^{-1}$ (NH$_4$)$_2$ SO$_4$, 3 g·L$^{-1}$ CaCO$_3$ and 0.05 g·L$^{-1}$ FeSO$_4$.
Culture Conditions
Fermentations were carried out in fermentors equipped with gas exhaust, stirrers, sampling ports, pH and temperature sensors. They were initiated by inoculation with 7.5% v/v seed culture.
The feeding vessel (1 L) was connected to the fermentor immediately after inoculation (FIG. 1). After 6 h when the butanol concentration was 1 g/L product removal through gas stripping with nitrogen was commenced at a gas flow rate 2 vvm N$_2$. The fed batch mode operation was started approximately 15 h after inoculation. The media reservoir pump was linked and activated once the sugar concentration in the vessel fell below the set value (26 g·L$^{-1}$). The medium reservoir supplied fresh sugar and nutrients. The feed pump ran automatically and intermittently depending on sugar uptake rate and culture growth. A control system was fitted to maintain temperature at 32±3° C. and minimum agitation (50-70 rpm). The pH was not controlled.
Analysis of Products and Substrates
As described for Example 1.
Results
FIG. 5 shows the accumulation of solvents (summation of solvents trapped outside and remaining within the fermentor) during the course of the fermentation. The final solvent titres obtained are much higher than those obtained in a conventional batch fermentation, i.e. Example 3.
FIG. 6 shows the correlation between solvent productivity and sugar uptake, and that peak solvent productivity has been extended by adding additional sugar during the fermentation and by removing solvents as they are produced. (The plotted data are cumulative averages.)
FIG. 7 shows a direct correlation between cell growth and density (measured by optical density) and solvent productivity. (The plotted data are cumulative averages.)
The solvent concentration value at which the fermentation was controlled was found to have a significant impact on growth rate and consequently the sugar uptake and solvent production rates. High solvent production rates were maintained for a prolonged period of time, through the feeding phase, suggesting the culture was growing at or close to its maximum growth rate. The fermentation was run for 164 hours, of which 53.5 h was with feeding. The solvent* productivities were 0.90 g/L/h during the feeding period and 0.79 g/L/h over the total fermentation period; the sugar uptake rates were 2.9 and 2.7 g/L/h, over the feeding and total fermentation periods, respectively; and the yields were 0.32 and 0.30 g solvents*/g sugar used, over the feeding and total fermentation periods, respectively. (*Note: 'solvents' data based on solvents collected—a significant portion of produced solvents were not trapped, so the actual values of solvent produced would be higher.)

Example 5: Fed Batch Fermentation on Glucose

Figure 8:
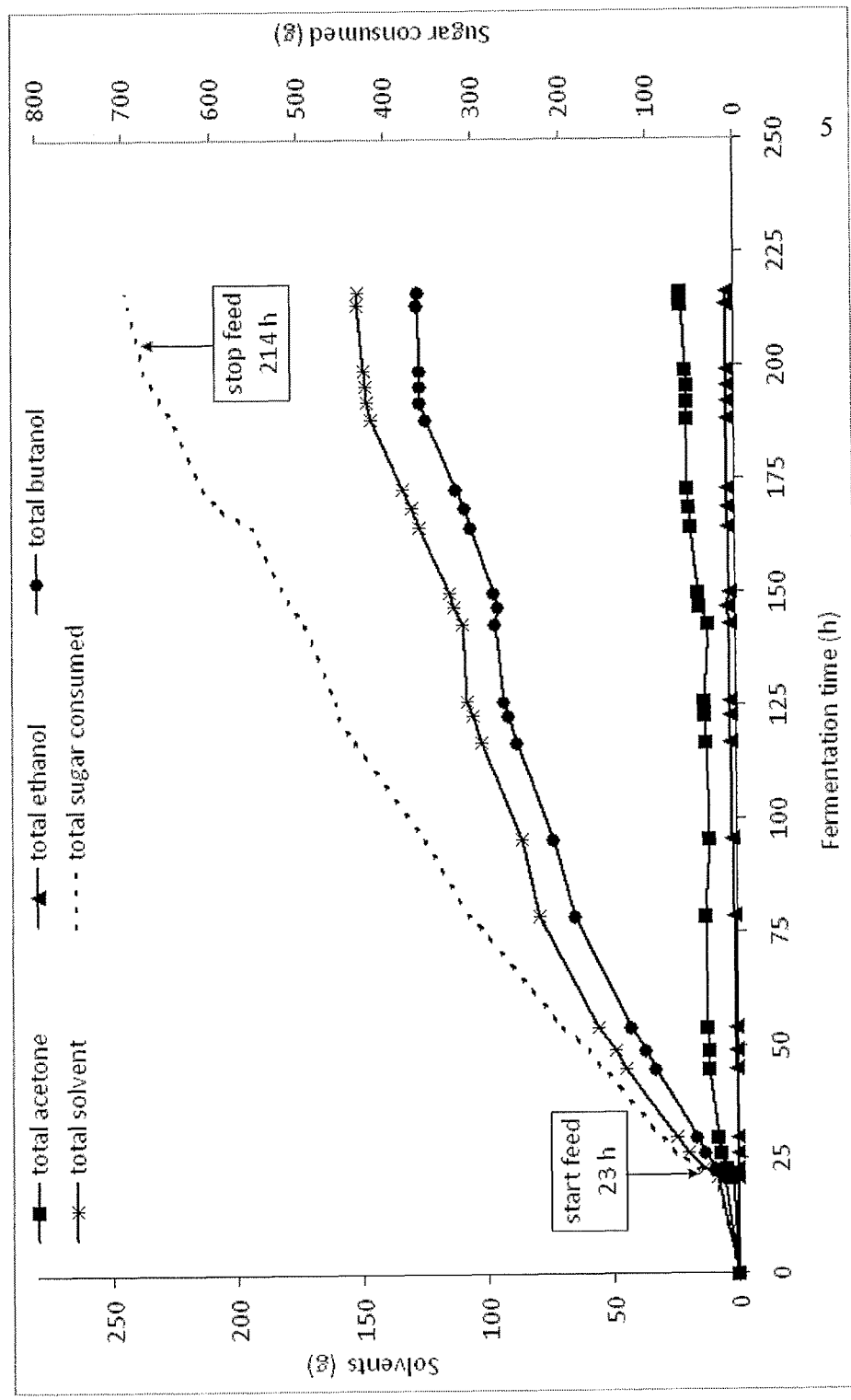
FIG. 8 is from a fed-batch fermentation with a monophasic solventogenic *clostridium*. Gas stripping was used to remove solvents and the sugar feed was glucose (Example 5). The graph shows the accumulation in solvents during the course of the fermentation.

Objective:
To demonstrate that the above fed batch system (Example 4) for cultivating monophasic solventogenic clostridia at high production rates also works using a different sugar source, e.g. crystallised glucose.
Materials and Methods
Bacterial Strain
A solventogenic *Clostridium saccharoperbutylacetonicum* strain N1-4(HMT) was cultured as described in Example 2.
Fermentation Medium
Crystallised glucose was the main carbon source for the fermentation medium. Experiments were carried at an initial volume of 1.55 L with starting sugar concentrations of 53 g·L$^{-1}$ in the fermentation vessel and supplemented with 2.5 g·L$^{-1}$ tryptone, 2.5 g·L$^{-1}$ yeast extract, 0.5 g·L$^{-1}$ (NH$_4$)$_2$SO$_4$, 0.025 g·L$^{-1}$ FeSO$_4$ and 3 g·L$^{-1}$ CaCO$_3$.
Feed Medium
650 mL of glucose solution at a concentration of 492 g·L$^{-1}$, with these nutrients: 3.8 g·L$^{-1}$ yeast extract, 3.8 g·L$^{-1}$ tryptone, 0.8 g·L$^{-1}$ (NH$_4$)$_2$SO$_4$, 0.05 g·L$^{-1}$ FeSO$_4$ and 3 g·L$^{-1}$ CaCO$_3$.
Sugar solutions and nutrient base media were batched and sterilised separately.
Culture Conditions
Fermentations were carried out in 2 L fermentors. The fermentors were equipped with gas exhaust, stirrers, sampling ports, pH and temperature sensors. They were initiated with the inoculation of 7.5% v/v seed culture. Inoculation with 7.5% v/v seed culture was repeated every 48 h.
The feeding vessel (1 L) was connected to the fermentor. Once the initial sugar concentration dropped below ~25 g/L, the feed addition (concentrated sugar plus nutrients) was started and product removal by gas stripping (≥2 vvm) was also started. The feed pump ran automatically and intermittently depending on sugar uptake rate and culture growth. A control system was fitted to maintain temperature at 32±1° C. and minimum agitation (50-70 rpm).
Analysis of Products and Substrates
As described for Example 1.
Results
The results are shown in FIG. 8. The graph shows the accumulation of solvents during the course of the fermentation. The fermentation was run for 216.5 hours, of which 191 h was with feeding. The solvent* productivities were 0.57 g/L/h during feeding period and 0.53 g/L/h over the total fermentation period; the sugar uptake rates were 2.1 and 2.0 g/L/h, over the feeding and total fermentation periods, respectively; and the yields were 0.21 and 0.20 g solvents*/g sugar used, over the feeding and total fermentation periods, respectively. (*Note: 'solvents' data based on solvents collected—a significant portion of produced solvents were not trapped, so the actual values of solvent produced would be higher.)

Example 6: Pilot Scale Fed Batch Fermentation on Glucose

Objective
To demonstrate that this fed batch fermentation process works at pilot scale, using glucose as the main sugar source.

This example system contains a membrane filtration unit (cell separator) that removes cells from the fermentation broth outside the culture vessel. The cells are recycled back into the culture vessel and the culture broth minus the cells is fed to a distillation column (solvent remover) that separates the solvents from the liquid culture medium. The distillate is returned to the culture vessel (see FIG. 1).

Bacterial Strain

A solventogenic *Clostridium saccharoperbutylacetonicum* strain N1-4(HMT) was cultured on 38 g·L$^{-1}$ Difco RCM Medium under anaerobic conditions at 32±1° C. for 16-18 h. 150 mL of this was used to inoculate a 5 L seed carboy containing rich glucose medium/seed (glucose 40 g/L, yeast extract 5 g/L, meat peptone 5 g/L, $(NH_4)_2SO_4$ 0.05 g/L, $FeSO_4$ 0.05 g/L and sodium acetate trihydrate 3 g/L). This was incubated for 5.25 h to generate 5 L of seed.

Fermentation Medium

Glucose was used as the main carbon source for the fermentation medium. 105 L of the following medium was prepared: glucose 60 g/L, yeast extract 2.5 g/L, meat peptone 2.5 g/L, $(NH_4)_2SO_4$ 2 g/L, $FeSO_4$ 0.05 g/L, corn oil 0.1% v/v, antifoam, (Suppressor 2343) 0.03 g/L.

Feed Media

50 L of concentrated sugar feed containing 450 g/L glucose.

16 L of nutrient addition solution comprising: yeast extract 58 g/L, meat peptone 58 g/L, $(NH_4)_2SO_4$ 17 g/L, FeSO4 0.4 g/L and corn oil 0.4% v/v.

Sugar solutions and nutrient base media were batched and sterilised separately.

Culture Conditions

Fermentations were carried out in 140 L fermentors, initially combining 105 L of fermentation medium with 5 L of seed.

Temperature was maintained at 30.5±0.3° C. The pH dropped quickly after inoculation until pH regulation started at pH 5.3 using 10-25% w/v NaOH.

Analysis of Products and Substrates

As described for Example 1.

Results

Figure 9:
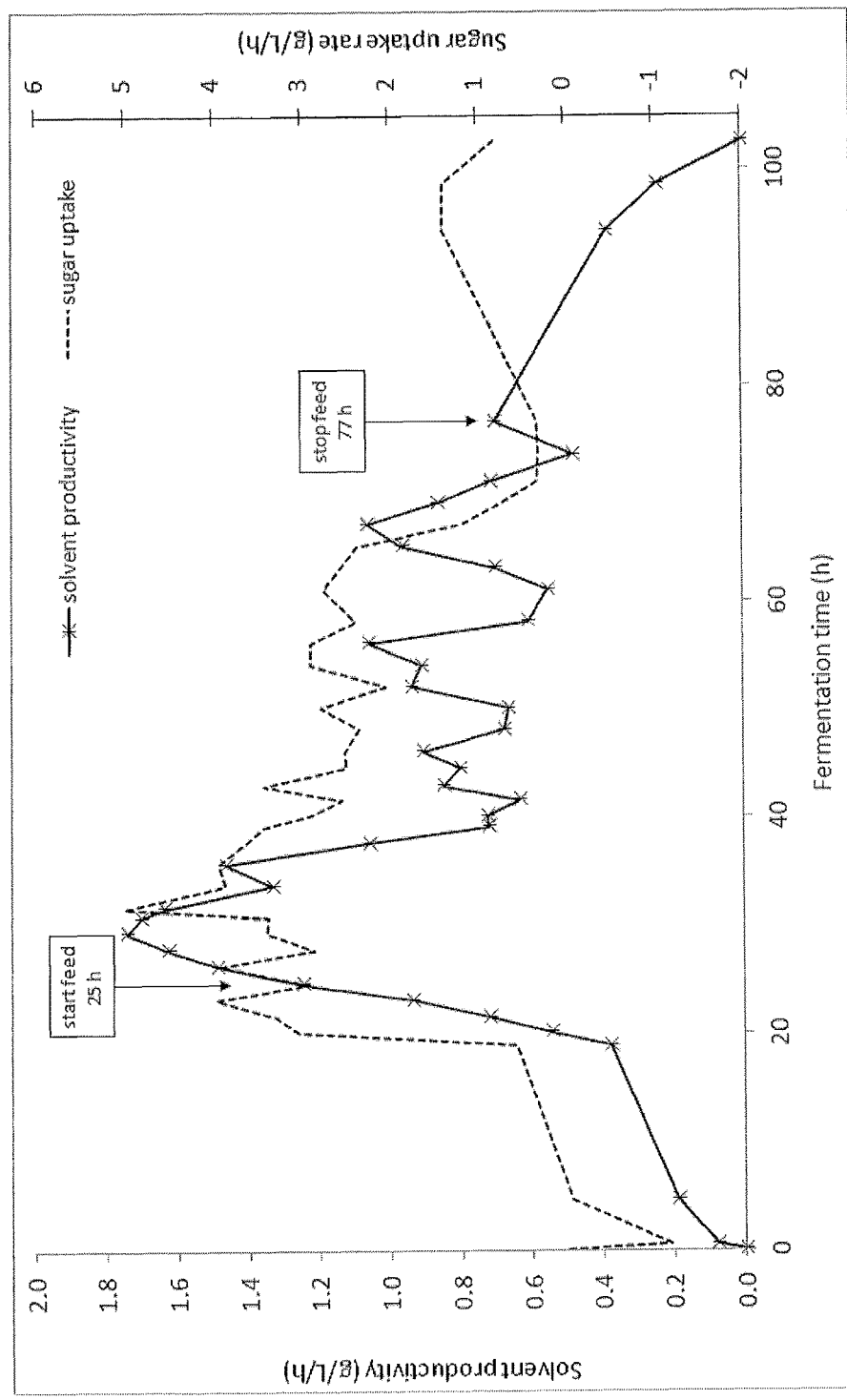
FIG. 9 is from a pilot-scale fed-batch fermentation with a monophasic solventogenic *clostridium*. The process contains a membrane filtration unit (cell separator) that removes cells from the fermentation broth outside the culture vessel. The cells are recycled back into the culture vessel and the culture broth minus the cells is fed to a distillation column (solvent remover) that separates the solvents from the liquid culture medium. The distillate is returned to the culture vessel. The sugar feed is glucose. The graph shows that high solvent productivity can be maintained for over 40 hours and that there is a direct correlation between sugar uptake and solvent production (Example 6).

The results are shown in FIG. 9. Plotted values are 5 point averages. The graph shows that high solvent productivity can be maintained for about 50 hours and that there is a direct correlation between sugar uptake and solvent production. The average productivity over whole 102.5 hour fermentation was 0.68 g/L/h, the productivity during 52 h fed-batch phase was 1.11 g/L/h, the sugar consumption over whole 102.5 hour fermentation was 1.91 g/L/h, the sugar consumption during 52 h fed-batch phase was 2.77 g/L/h, the solvent production based on 120 L final volume was 70 g/L, the ABE yield on sugars consumed was 35.7% and the butanol ratio was 76%.

Example 7: Pilot Scale Fed Batch Fermentation on Clarified Corn Mash

Objective

To demonstrate that this fed batch fermentation process works at pilot scale, using clarified corn mash as the main sugar source. This example system contains a membrane filtration unit (cell separator) that removes cells from the fermentation broth outside the culture vessel. The cells are recycled back into the culture vessel and the some of the cell-free culture broth is fed to a distillation column (solvent remover) that separates the solvents from the liquid culture medium. The stillage is returned to the culture vessel (see FIG. 1).

Bacterial Strain

A solventogenic *Clostridium saccharoperbutylacetonicum* strain N1-4(HMT) was cultured on 38 g·L$^{-1}$ Difco RCM Medium under anaerobic conditions at 32±1° C. for 16-18 h. 150 mL of this was used to inoculate 5 L containing rich clarified corn mash medium/seed (clarified corn mash equivalent to 40 g/L sugars, yeast extract 5 g/L, meat peptone 5 g/L, $(NH_4)_2SO_4$ 2 g/L, $FeSO_4$ 0.05 g/L and sodium acetate trihydrate 3 g/L). This was incubated for 5.25 h to generate 5 L of seed.

Fermentation Medium

Clarified corn mash was used as the main carbon source for the fermentation medium. 105 L of the following medium was prepared: clarified corn mash equivalent to 60 g/L sugar, yeast extract 2.5 g/L, $(NH_4)_2SO_4$ 2 g/L and $FeSO_4$ 0.05 g/L.

Feed Media

75 L of concentrated sugar feed containing clarified corn mash equivalent to 270 g/L sugar.

8 L of nutrient addition solution comprising: yeast extract 95 g/L, $(NH_4)_2SO_4$ 65 g/L and $FeSO_4$ 1.7 g/L.

Sugar solutions and nutrient base media were batched and sterilised separately.

Culture Conditions

Fermentations were carried out in 140 L fermentors, initially combining 100 L of fermentation medium with 5 L of seed.

Temperature was maintained at 30.5±0.3° C. The pH dropped quickly after inoculation until pH regulation started at pH 5.3 using 10-25% w/v NaOH.

Analysis of Products and Substrates

As described for Example 1.

Results

Figure 10:
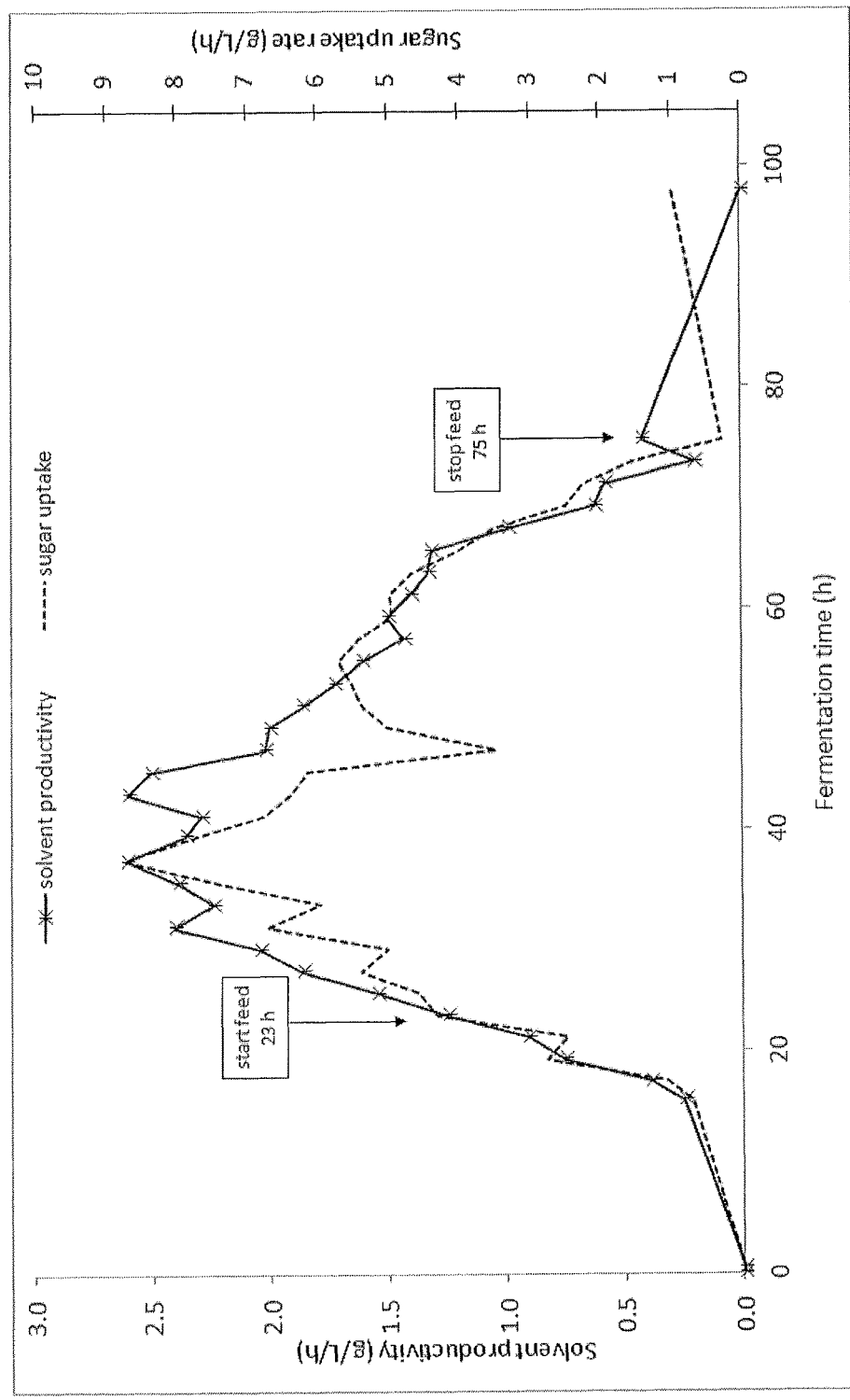
FIG. 10 is from a pilot scale fed-batch fermentation with a monophasic solventogenic *clostridium*. The process contains a membrane filtration unit (cell separator) that removes cells from the fermentation broth outside the culture vessel. The cells are recycled back into the culture vessel and the culture broth minus the cells is fed to a distillation column (solvent remover) that separates the solvents from the liquid culture medium. The distillate is returned to the culture vessel. The sugar feed is corn mash. The graph shows that high sugar uptake and solvent productivity can be maintained for over 40 hours using an industrial corn based feedstock (Example 7).

The results are shown in FIG. 10. Plotted values are 5 point averages. The graph shows that high sugar uptake and solvent productivity can be maintained for about 50 hours using an industrial corn based feedstock.

The average productivity over the 110 hour fermentation cycle (97.75 h fermentation+CIP (cleaning in place) time+turnaround time) was 0.87 g/L/h, the productivity during 52 h fed-batch phase was 1.51 g/L/h, the sugar consumption over the 110 hour fermentation cycle was 2.84 g/L/h, the sugar consumption during 52 h fed-batch phase was 5.25 g/L/h, the solvent production based on 105 L final volume was 96 g/L, the ABE yield on sugars consumed was 30.6% and the butanol ratio was 61.5%.

Example 8: Pilot Scale Fed Batch Fermentation on Molasses, with Gas Production Monitoring Objective To demonstrate that this fed batch fermentation process works at pilot scale, using molasses as the main sugar source. This example system contains a membrane filtration unit (cell separator) that removes cells from the fermentation broth outside the culture vessel. The cells are recycled back into the culture vessel and the culture broth minus the cells is fed to a distillation column (solvent remover) that separates the solvents from the liquid culture medium. The distillate is returned to the culture vessel (see FIG. 1). Additionally, gases from the fermentation are monitored.

Bacterial Strain

A solventogenic *Clostridium saccharoperbutylacetonicum* strain N1-4(HMT) was cultured on 38 g·L$^{-1}$ Difco RCM Medium under anaerobic conditions at 32±1° C. for 16-18 h. 150 mL of this was used to inoculate 5 L containing rich molasses medium/seed (molasses equivalent to 35 g/L sugars, yeast extract 5 g/L, meat peptone 5 g/L, $(NH_4)_2SO_4$ 2 g/L, $FeSO_4$ 0.05 g/L and sodium acetate trihydrate 3 g/L). This was incubated for 5.25 h to generate 5 L of seed.

Fermentation Medium

Sugar cane molasses was used as the main carbon source for the fermentation medium. 105 L of the following medium was prepared: sugar cane molasses equivalent to 50 g/L sugar, yeast extract 2.5 g/L, meat peptone 2.5 g/L, $(NH_4)_2SO_4$ 2 g/L, $FeSO_4$ 0.05 g/L, corn oil 0.1% v/v and antifoam (Suppressor 2343) 0.03 g/L.

Feed Media

50 L of concentrated sugar feed containing sugar cane molasses equivalent to 350 g/L sugar.

16 L of nutrient addition solution comprising: yeast extract 34 g/L, meat peptone 34 g/L, $(NH_4)_2SO_4$ 20 g/L, $FeSO_4$ 0.5 g/L and corn oil 0.6%.

Sugar solutions and nutrient base media were batched and sterilised separately.

Culture Conditions

Fermentations were carried out in 140 L fermentors, initially combining 105 L of fermentation medium with 5 L of seed.

Temperature was maintained at 30.5±0.3° C. No calcium carbonate or other buffering agent was added. The pH dropped quickly after inoculation until pH regulation started at pH 5.3 using 10-25% w/v NaOH.

The butanol concentration in the culture vessel was kept below 6 g/l, and the sugar concentration in the culture vessel was maintained between 20 and 30 g/L during the feeding.

Analysis of Products and Substrates

As described for Example 1.

Results

Figure 11:
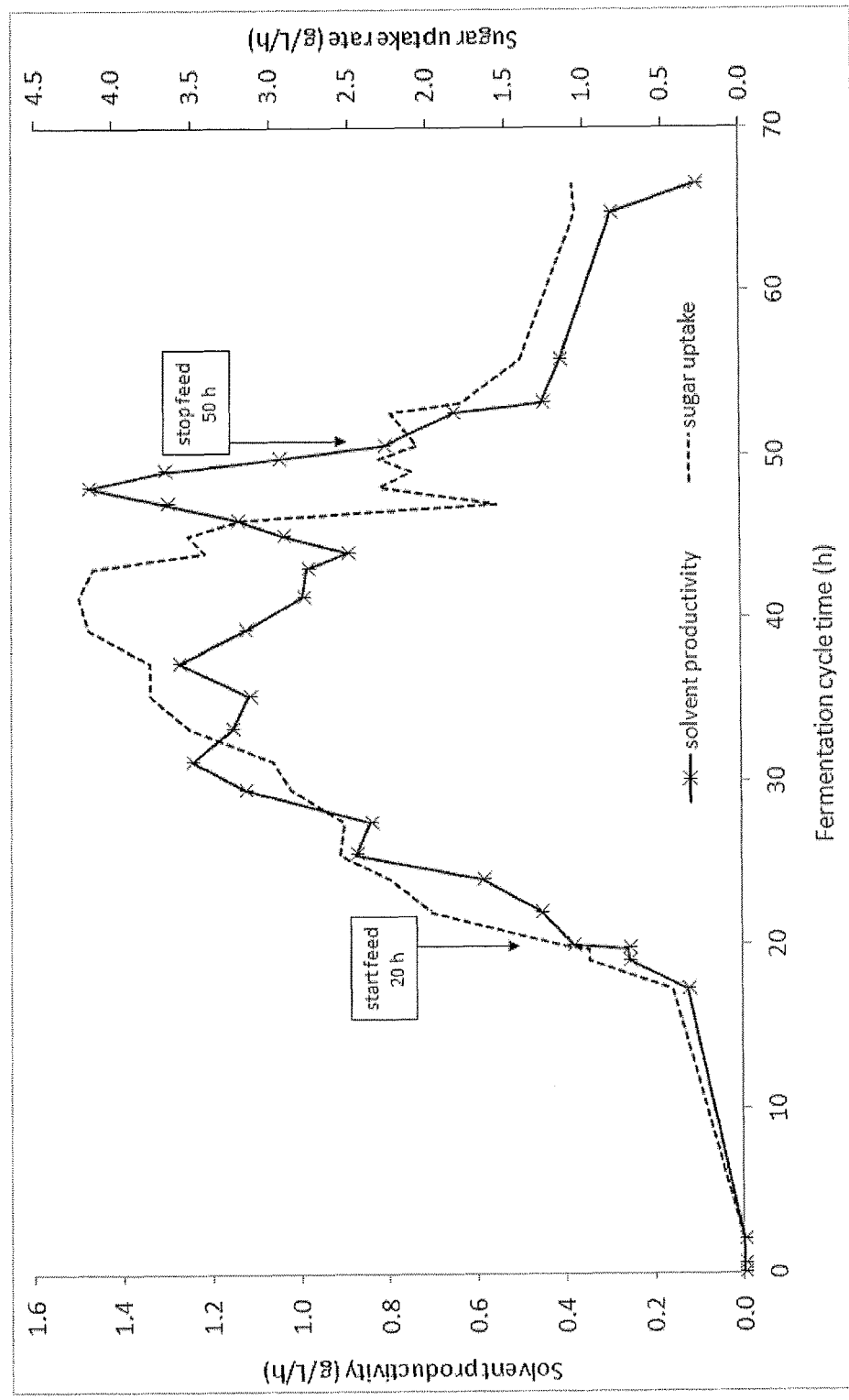
FIG. 11 is from a pilot scale fed-batch fermentation with a monophasic solventogenic *clostridium*. The process contains a membrane filtration unit (cell separator) that removes cells from the fermentation broth outside the culture vessel. The cells are recycled back into the culture vessel and the culture broth minus the cells is fed to a distillation column (solvent remover) that separates the solvents from the liquid culture medium. The distillate is returned to the culture vessel. The sugar feed is molasses. The graph shows the correlation between sugar uptake and solvent productivity during the fermentation (Example 8).
Figure 12:
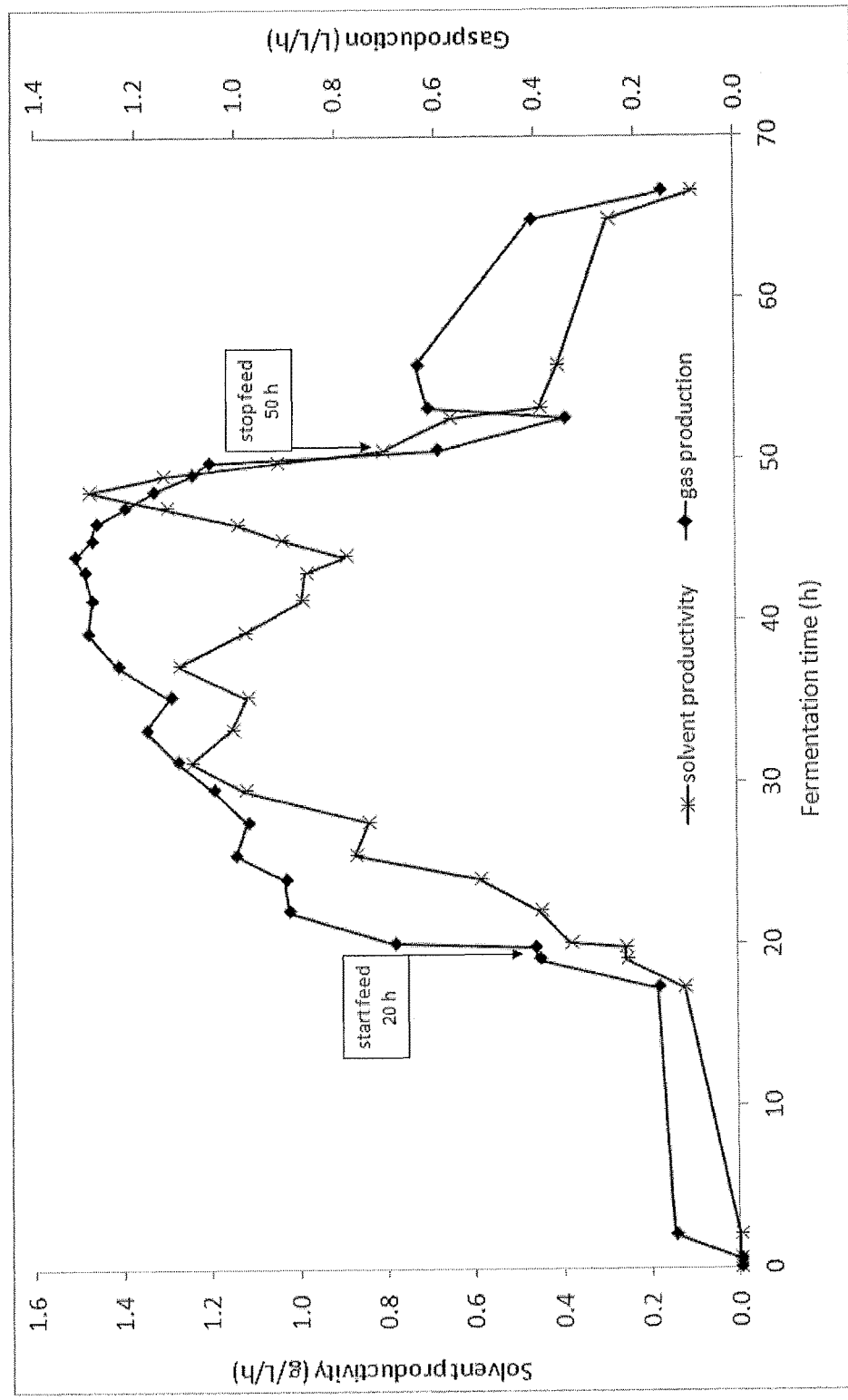
FIG. 12 is from a pilot scale fed-batch fermentation with a monophasic solventogenic *clostridium*. The process contains a membrane filtration unit (cell separator) that removes cells from the fermentation broth outside the culture vessel. The cells are recycled back into the culture vessel and the culture broth minus the cells is fed to a distillation column (solvent remover) that separates the solvents from the liquid culture medium. The distillate is returned to the culture vessel. The sugar feed is molasses. The graph shows the correlation between gas production and solvent productivity during the fermentation (Example 8).

The results are shown in FIGS. 11 and 12. Plotted values are 5 point averages. FIG. 11 shows the correlation between sugar uptake and solvent productivity during the fermentation, indicating that high sugar uptake and solvent productivity can be maintained for a prolonged period using an industrial molasses-based feedstock. FIG. 12 shows the correlation between gas production and solvent productivity during the fermentation.

The average productivity over the 67 hour fermentation was 0.60 g/L/h, the productivity during the 30 h fed-batch phase was 0.95 g/L/h, the sugar consumption over the 67 hour fermentation was 1.67 g/L/h, the sugar consumption during the 30 h fed-batch phase was 2.74 g/L/h, the ABE yield on sugars consumed was 35.8% and the butanol ratio was 75%.

The invention claimed is:

1. A single-stage fed-batch or single-stage continuous process for the production of one or more solvents, the process comprising the steps:
    (a) culturing cells of a monophasic solventogenic *Clostridium saccharoperbutylacetonicum* cells in a liquid culture medium in a culture vessel and producing one or more solvents in the same vessel;
    (b) monitoring cell growth of the monophasic solventogenic *Clostridium saccharoperbutylacetonicum* cells in the culture vessel;
    (c) continuously or semi-continuously introducing fresh culture media and/or nutrients into the culture vessel;
    (d) continuously or semi-continuously removing a stream or portion of liquid culture medium comprising solvent(s) from the culture vessel and passing said liquid culture medium to a solvent remover to extract the one or more solvents;
    (e) maintaining or increasing cell density within the culture vessel; wherein cell growth in the culture vessel is regulated and/or optimized by controlling:
        (i) the amount or rate of fresh culture medium or nutrients which are introduced into the culture vessel, and/or
        (ii) the amount or rate of liquid culture medium comprising one or more solvents which is removed from the culture vessel.

2. The process as claimed in claim 1, wherein step (e) comprises:
    increasing cell density within the culture vessel;
        wherein cell growth in the culture vessel is optimized by controlling:
            (i) the amount or rate of fresh culture medium or nutrients which are introduced into the culture vessel, and/or
            (ii) the amount or rate of liquid culture medium comprising one or more solvents which is removed from the culture vessel,
    wherein the process maintains cell growth and optimizes cell density within the culture vessel, and maximizes sugar utilization and solvent production.

3. The process as claimed in claim 1, wherein the monophasic solventogenic *Clostridium saccharoperbutylacetonicum* cells:
    (a) naturally display simultaneous growth and solvent production during the major growth phase of batch fermentations;
    (b) have been chemically mutated to produce solvents during growth; or
    (c) have been genetically modified to produce solvents during growth.

4. The process as claimed in claim 3, wherein the monophasic *Clostridium saccharoperbutylacetonicum* is a monophasic *Clostridium saccharoperbutylacetonicum* N1 strain.

5. The process as claimed in claim 1, wherein step (b) comprises monitoring cell growth by one or more of:
    (i) monitoring production of one or more gases;
    (ii) monitoring production of one or more acids;
    (iii) monitoring the pH of the culture medium;
    (iv) monitoring the utilization of sugar;
    (v) monitoring cell density; and
    (vi) monitoring the production of one or more solvents.

6. The process as claimed in claim 1, wherein in step (b) the monitored level of cell growth is compared to a reference level and fresh media or nutrients are introduced into the culture vessel and/or liquid media comprising solvents are removed from the culture vessel if the monitored level is lower than the reference level.

7. The process as claimed in claim 1, wherein step (d) comprises continuously or semi-continuously removing a stream or portion of the liquid culture medium from the culture vessel and passing the stream/portion via a cell separator to the solvent remover.

8. The process as claimed in claim 1, wherein the one or more solvents is extracted continuously.

9. The process as claimed in claim 1, wherein in step (d) liquid culture medium comprising one or more solvents is removed from the culture vessel at a rate which maintains the solvent concentration in the liquid culture below a defined solvent concentration point, wherein the concentration point is the toxicity threshold of that solvent for the monophasic solventogenic *Clostridium saccharoperbutylacetonicum*.

10. The process as claimed in claim 9, wherein the solvent is butanol and wherein the defined solvent concentration point is 8-10 g butanol/L.

11. The process as claimed in claim 1, wherein the solvent is butanol and wherein the butanol concentration in the culture vessel does not exceed 10 g/L.

12. The process as claimed in claim 1, wherein in step (e) the cell density is maintained or increased within the culture vessel by:
   (i) recycling cells which are removed from the liquid culture medium comprising one or more solvents back to the culture vessel; and/or
   (ii) continuously or semi-continuously feeding cells from a cell seeder into the culture vessel; and/or
   (iii) immobilization of some or all of the cells within the culture vessel.

13. The process as claimed in claim 1, wherein the liquid culture medium comprises sugar and wherein the amount of sugar in the liquid culture medium is maintained at 5-30 g/L.

14. The process as claimed in claim 1, wherein the monophasic solventogenic *Clostridium saccharoperbutylacetonicum* cells are cultured in the liquid culture medium in the culture vessel with no prior anaerobic purge.

15. The process as claimed in claim 4, wherein the monophasic solventogenic *Clostridium saccharoperbutylacetonicum* N1 strain is:

(i) *Clostridium saccharoperbutylacetonicum* N-1(HMT) deposited under accession number ATCC 27021 or *Clostridium saccharoperbutylacetonicum* N1-504 deposited under accession number ATCC 27022; or a monophasic and solventogenic variant or derivative thereof.

16. The process as claimed in claim 7, wherein:
   (i) cells are removed from the liquid culture medium in the cell separator and the cells are returned to the culture vessel (optionally via a cell seeder), and/or
   (ii) wherein solvent is removed from the liquid culture medium in the solvent remover and the residual liquid culture medium is returned to the culture vessel.

17. A process as claimed in claim 1, wherein the solvent is butanol.

18. A process as claimed in claim 1, wherein the process is a single-stage fed-batch process.

19. A process as claimed in claim 1, wherein the process is a single-stage continuous process.

* * * * *